(12) United States Patent
Goeders

(10) Patent No.: US 9,415,107 B2
(45) Date of Patent: *Aug. 16, 2016

(54) COMPOSITIONS AND METHODS FOR THE TREATMENT OF ADDICTION AND OTHER NEUROPSYCHIATRIC DISORDERS

(75) Inventor: Nicholas E. Goeders, Shreveport, LA (US)

(73) Assignee: Board Of Supervisors Of Louisiana State University & Agricultural & Mechanical College, Baton Rouge, LA (US)

( * ) Notice: Subject to any disclaimer, the term of this patent is extended or adjusted under 35 U.S.C. 154(b) by 773 days.

This patent is subject to a terminal disclaimer.

(21) Appl. No.: 12/093,048

(22) PCT Filed: Nov. 13, 2006

(86) PCT No.: PCT/US2006/044126
§ 371 (c)(1),
(2), (4) Date: Nov. 18, 2008

(87) PCT Pub. No.: WO2007/056618
PCT Pub. Date: May 18, 2007

(65) Prior Publication Data
US 2009/0203669 A1    Aug. 13, 2009

Related U.S. Application Data

(60) Provisional application No. 60/735,507, filed on Nov. 10, 2005, provisional application No. 60/764,727, filed on Feb. 2, 2006.

(51) Int. Cl.
*A01N 43/00* (2006.01)
*A61K 31/33* (2006.01)
*A61K 45/06* (2006.01)
*A61K 31/444* (2006.01)
*A61K 31/496* (2006.01)
*A61K 31/4985* (2006.01)
*A61K 31/5513* (2006.01)

(52) U.S. Cl.
CPC .............. *A61K 45/06* (2013.01); *A61K 31/444* (2013.01); *A61K 31/496* (2013.01); *A61K 31/4985* (2013.01); *A61K 31/5513* (2013.01)

(58) Field of Classification Search
USPC ........................................................ 514/183
See application file for complete search history.

(56) References Cited

U.S. PATENT DOCUMENTS 4,594,329 A  6/1986  Vale, Jr.
4,605,642 A  8/1986  Rivier
4,661,493 A  4/1987  Gibbs
4,814,333 A  3/1989  Ravaris
4,925,844 A * 5/1990  Resch ............................ 514/248
4,942,162 A  7/1990  Rosenberg
5,016,655 A  5/1991  Waddell
5,456,850 A  10/1995 Trabitzsch
5,869,474 A * 2/1999  Goeders ........................ 514/171
6,323,312 B1 11/2001 Rivier
6,326,463 B1 12/2001 Rivier
9,078,886 B2  7/2015  Goeders
2002/0078969 A1  6/2002  Wastchak et al.
2003/0211157 A1  11/2003  Simon
2004/0092481 A1* 5/2004  Jerussi ............................ 514/58
2004/0204401 A1  10/2004 Migaly
2005/0037983 A1  2/2005  Dinan
2005/0090553 A1  4/2005  Shapiro
2005/0203130 A1  9/2005  Buntinx
2005/0215533 A1  9/2005  Gottlieb
2008/0206138 A1  8/2008  Zolle et al.
2013/0303523 A1  11/2013 Goeders

FOREIGN PATENT DOCUMENTS

EP       393942 A1   10/1990
EP    1 666 468 A1   6/2006
JP    2005-519850 A  7/2005
JP   WO 2005/061508 A1  7/2005
WO      WO 91/00906 A1  1/1991
WO      WO 00/54766    9/2000

(Continued)

OTHER PUBLICATIONS

Brown et al. ("Ketoconazole Inhibits Chlordiazepoxide (Cdx) Clearance in Man-Differences in Acute and Chronic Treatment." In Hepatology, vol. 4, No. 5, pp. 1036-1036, 1984).*
Bech et al. ("A case of sequential anti-stress medication in a patient with major depression resistant to amine-reuptake inhibitors." Acta Psychiatrica Scandinavica 100.1 (1999): 76-78).*
De Souza, Errrol B., "Neuroendoctrine Effects of Benzodiazepines", J. Psychiat. Res., vol. 24, suppl. 2, 1990, pp. 111-119.
Zhang et al., "Interactions of Corticotropin-Releasing Factor with Antidepressant and Anxiolytic Drugs" Behavioral Studies with Pigeons, Biol. Psychiatry, vol. 27, 1990, pp. 953-967.

(Continued)

*Primary Examiner* — Layla Soroush
(74) *Attorney, Agent, or Firm* — Wolf, Greenfield & Sacks, P.C.

(57) ABSTRACT

The present invention is based, in part, on our discovery that certain types of therapeutic agents can be used in combination to treat a variety of neuropsychiatric and related disorders, including addiction (e.g., to a substance or to an activity) as well as to alleviate some of the symptoms experienced during menopause or associated with the menstrual cycle. Regardless of the precise formulation, the compositions of the invention can include at least one active ingredient that targets the hypothalamo-pituitary-adrenal (HPA) axis and at least one active ingredient that targets the prefrontal cortex. Either or both of these types of agents can be combined with an agent that inhibits activity in the sympathetic nervous system. Thus, the compositions or combination pharmacotherapies can also include an agent that inhibits a beta-adrenergic receptor or that otherwise acts as an anti-hypertensive or anxiolytic agent.

12 Claims, 16 Drawing Sheets

(56) References Cited

FOREIGN PATENT DOCUMENTS

| | | |
|---|---|---|
| WO | WO 01/52833 | 7/2001 |
| WO | WO 2004/032916 | 4/2004 |
| WO | WO 2005/026126 A1 | 3/2005 |
| WO | WO 2005/100992 A1 | 10/2005 |
| WO | WO 2007/056618 A1 | 5/2007 |
| WO | WO 2007/100775 | 9/2007 |

OTHER PUBLICATIONS

Arvat, et al., "The inhibitory effect of alprazolam, a benzodiazepine, overrides the stimulatory effect of metyrapone-induced lack of negative cortisol feedback on corticotroph secretion in humans", The Journal of Clinical Endocrinology & Metabolism, vol. 84, No. 8, 1999, pp. 2611-2615.

Contoreggi, et al., "Stress hormone responses to corticotrophin-releasing hormone in substance abusers without severe comorbid psychiatric disease", Biological Psychiatry, vol. 54, No. 9, Nov. 2003, pp. 873-878.

Goldstein and Volkow, "Drug addiction and its underlying neurobiological basis: neuroimaging evidence for the involvement of the frontal cortex", American Journal of Psychiatry, vol. 159, No. 10, Oct. 2002, pp. 1642-1652.

International Search Report from corresponding PCT Application No. PCT/US2006/044126, mailed Mar. 8, 2007, 4 pages.

Guerin et al., "Combination pharmacotherapy targeting the HPA axis and its effects on cocaine self-administration in rats", Society for Neuroscience Annual Meeting, Abstract No. 978.3, Nov. 15, 2001, San Diego, CA.

Murphy et al., "Response to Steroid Suppression in Major Depression Resistant to Antidepressant Therapy", Journal of Clinical Psychopharmacology, 11(2):121-126, 1991.

Piazza et al., "Inhibition of Corticosterone Synthesis by Metyrapone Decreases Cocaine-Induce Locomotion and Relapse of Cocaine Self-Administration", Brain Research, 658:259-264, 1994.

Patel et al., "Endocannabinoid Signaling Negatively Modulates Stress-Induced Activation of Hypothalamic-Pituitary-Adrenal Axis", Endocrinology, 145(12):5431-5438, 2004.

Peltier et al., "Effects of Saline Substitution on Responding and Plasma Corticosterone in Rats Trained to Self-Administer Different Doses of Cocaine", The Journal of Pharmacology and Experimental Therapeutics, 299:114-120, 2001.

Perry-O'Keefe et al., "Peptide Nucleic Acid Pre-Gel Hybridization: An Alternative to Southern Hybridization", Proceedings of the National Academy of Sciences, USA, 93:14670-14675, 1996.

Rivier et al., "Synthetic Competitive Antagonists of Corticotropin-Releasing Factor: Effect on ACTH Secretion in the Rat", Science, 224:889, 1984.

Shaham et al., "Strss-Induced Relapse to Heroine and Coaine Seeking in Rats: A Review", Brain Reseach Reviews 33:13-33, 2000.

Sinha, "How Does Stress Increase Risk of Drug Abuse and Relapse?", Psychopharmacology, 158:343-359, 2001.

Smagin and Goeders, "Effects of Acute and Chronic Ketoconazole Administration on Hypothalamo-Pituitary-Adrenal Axis Activity and Brain Corticotropin-Releasing Hormone", Psychoneuroendocrinology, 29:1223-1228, 2004.

Sonino, IN Agarwal (ED), "Inhibition of Adrenal Steroid Biosynthesis by Metyrapone, Hormone Antagonists", Walter de Gruyter & Co., Berlin—New York, pp. 421-429, 1982.

Sonino, "The Use of Ketoconazole as an Inhibitor of Steroid Production", The New England Journal of Medicine, 317 (13):812-818, 1987.

Stewart "Pathways to Relapse: The Neurobiology of Drug- and Stress-Induced Relapse to Drug-Taking", Journal of Psychiatry and Neuroscience, 25(2):125-136, 2000.

Tanaka et al., "Sequence-Specific Interaction of α • β-anoneric Double-Stranded DNA with the p50 Subunit of NFxB: Application to the Decoy Approach", Nucleic Acids Research, 22(15):3069-3074, 1994.

Tarr and Macklin, "Chemical Dependency", Pediatric Clinics of North America, 34(2):319-331, 1987.

Tasker, "Endogenous Cannabinoids Take the Edge Off Neuroendocrine Responses to Stress", Endocrinolology, 145(12):5429-5430, 2004.

Thienpont et al., "Ketoconazole—A New Broad Spectrum Orally Active Antimycotic", Experientia, 35:606-607, 1979.

Thomas et al., "Comparative Receptor Binding Analyses of Cannabinoid Agonists and Antagonists", The Journal of Pharmacology and Experimental Therapeutics, 285(1):285-292, 1998.

Toulmé, "New Candidates for True Antisense", Nature Biotechnology, 19:17, 2001.

Wolkowitz et al., "Ketoconazole Administration in Hypercortisolemic Depression", American Journal of Psychiatry, 150:810-812, 1993.

Mantsch and Goeders, "Ketoconazole Does Not Block Cocaine Discrimination of the Cocaine-Induced Reinstatement of Cocaine-Seeking Behavior", Pharmacology Biochemistry and Behavior, vol. 64, No. 1, pp. 65-73.

Perault-Staub et al., "Thyroid Function and Plasma Phosphate Level in Rat", Endocrinology, 90:558-562, 1972.

Baldessarini, "Drugs and the Treament of Psychiatric Disorder", In: Hardman et al. (Eds), Goodman & Gilman's The Pharmacological Basis of Therapeutics, McGraw-Hill, New York, pp. 399-430, 1996.

Baumann et al., "Effects of Intravenous Cocaine on Plasma Cortisol and Prolactin in Human Cocaine Abusers", Biol. Psych., 38:751-755, 1995.

Chesley et al., "Cocaine Augments Peripheral Benzodiazepine Binding in Humans", Journal of Clinical Psychiatry, 51:404-406, 1990.

Crowley, In: Fisher et al. (Eds), Cocaine: Clinical and Biobehavioral Aspects, Oxford University Press, New York, pp. 193-211, 1987.

De Wit, "Priming Effects With Drugs and Other Reinforcers", Experimental and Clinical Psychopharmacology, 4(1):5-10, 1996.

Di Paolo et al., "Endocrine and Neurochemical Actions of Cocaine", Canadian Journal of Physiology and Pharmacology, 67:1177-1181, 1989.

Elman et al., "Acute Cortisol Administration Triggers Craving in Individuals with Cocaine Dependence", Psychopharmacology Bulletin, 37(3):84-89, 2003.

Engelhardt et al., "Ketoconazole Blocks Cortisol Secretion in Man by Inhibition of Adrenal 11β-Hydroxylase", Klinische Wochenschrift, 63:607-612, 1985.

Faria et al., "Phosphoramidate Oligonucleotdes as Potent Antisense Molecules in Cells and In Vivo", Nature Biotechnology, 19:40-44, 2001.

Gautier et al., "Alpha-DNA IV: Alpha-anomeric and Beta-anomeric Tetrathymidylates Covalently Linked to Intercalating Oxazolopyridocarbazole: Synthesis, Physiochemical Properties and Poly (rA) Binding", Nucleic Acids Research, 15(16):6625-6641, 1987.

Gawin and Ellinwood, "Cocaine Dependence", Ann. Rev. Med., 40:149-161, 1989.

Gay, "You've Come a Long Way, Baby! Coke Time for the New American Lady of the Eighties", Journal of Psychoactive Drugs, 13(4):297-318, 1981.

Ghadirian et al., "The Psychotropic Effects of Inhibitors of Steroid Biosynthesis in Depressed Patients Refractory to Treatment", Biological Psychiatry, 37:369-375, 1995.

Goeders and Guerin, "Non-Contingent Electric Footshock Facilitates the Acquisition of Intravenous Cocaine Self-Administration in Rats", Psychopharmacology, 114:63-70, 1994.

Goeders et al., "Role of Corticosterone in Intravenous Cocaine Self-Administration in Rats", Neuroendocrinology, 64:337-348, 1996.

Goeders et al., "Effects of Surgical and Pharmacological Adrenalectomy on the Initiation and Maintenance of Intravenous Cocaine Self-Administration in Rats", Brain Research, 722:145-152, 1996.

Goeders et al., "Effects of Ketoconazole on Intravenous Cocaine Self-Administration in Rats", Abstract submitted to the 58th Annual Scientific Meeting of the College on Problems of Drug Dependence (CPDD), Jun. 22-27, 1996 (Abstract only).

Goeders, "A Neuroendocrine Role in Cocaine Reinforcement", Psychoneuroendocrinology, 22(4):237-259, 1997.

Lucinio et al., "The Hypothalamic-Pituitary-Adrenal Axis in Anorexia Nervosa", Psychiatry Research, 62:75-83, 1996.

(56) References Cited

OTHER PUBLICATIONS

Goeders et al., "Ketoconazole Reduces Low Dose Cocaine Self-Administration in Rats", Drug and Alcohol Dependence, 53:67-77, 1998.
Goeders and Guerin, "Effects of the CRH Receptor Antagonist CP-154,526 on Intravenous Cocaine Self-Administration in Rats", Neuropsychopharmacology, 23(5):577-586,2000.
Goeders, "Stress and Cocaine Addiction", Journal of Pharmacology and Experimental Therapeutics, 301(3):785-789, 2002.
Goeders, "The HPA Axis and Cocaine Reinforcement", Psychoneuroendocrinology, 27:13-33, 2002.
Goeders and Clampitt, "Poential Role for the Hypothalamo-Pituitary-Adrenal Axis in the Conditoned Reinforcer-Induced Reinstatement of Extinguished Cocaine Seeking in Rats", Psycpharmacology, 161:222-232, 2002.
Goeders, "The Impact of Stress on Addiction", European Neuropsychopharmacology, 13:435-441, 2003.
Goeders, "Stress, Motivation, and Drug Addiction", Current Directions in Psychological Science, 13(1):33-35, 2004.
Goeders and Goeders, "Effects of Oxazepam on Methamphetamine-Induced Conditioned Place Preference", Pharmacology Biochemistry and Behavior, 78:185-188, 2004.
Gurkovskaya and Goeders, "Effects of CP-154,526 on Responding During Extinction from Cocaine Self-Administration in Rats", European Journal of Pharmacology, 432:53-56, 2001.
Haleem et al., "Adaptation of Female Rats to Stress: Shift to Male Pattern by Inhibition of Corticosterone Synthesis", Brain Research, 458:339-347, 1988.
Haynes, In: Gilman et al. (Eds), Adrenocorticotropic Hormone; Adrenocortical Steroids and Theft Synthetic Analogs; Inhibitors of the Synthesis and Actions of Adrenocortical Hormones, The Pharmacological Basis of Therapeutics, eighth edition, Pergamon Press, New York, pp. 1431-1462, 1990.
Heesch et al., "Effects of Cocaine on Cortisol Secretion in Humans", American Journal of Medical Sciences, 310:61-64, 1995.
Hélène, "The Anti-Gene Strategy: Control of Gene Expression by Triplex-Forming-Oligonucleotides", Anti-Cancer Drug Design, 6(6):569-584, 1991.
Hélène et al., "Control of Gene Expression by Triple Helix-Forming Oligonucleotides", The Antigene Strategy, Annals New York Academy of Sciences, 660:27-36, 1992.
Hyrup et al., "Peptide Nucleic Acids (PNA): Synthesis, Properties and Potential Applications", Bioorganic & Medicinal Chemistry, 4(1):5-23, 1996.
Inoue et al., "Synthesis and Hybridization Studies on Two Complementary Nona(2'-O-methyl)ribonucleotides", Nucleic Acids Research, 15(15):8131-8148, 1987.
Inoue et al., "Sequence-Dependent Hydrolysis of RNA Using Modified Oligonucleotide Splints and RNase H", Federation of European Biochemical Societies Letters, 215(2):327-330, 1987.
Javaid et al., "Peripheral Eienzodiazepine Receptors Are Decreased During Cocaine Withdrawal in Humans", Biological Psychiatry, 36:44-50, 1994.
Joëls et al., "Mineralocorticoid and Glucocorticoid Receptors in the Brain. Implications for Ion Permeability and Transmitter Systems", Progress in Neurobiology, 43:1-36, 1994.
Kleber, "Pharmacotherapy, Current and Potential, for the Treatment of Cocaine Dependence, Clinical Neuropharmacology", 18(Suppl. 1):S96-S109, 1996.
Lamon and Alonzo, "Stress Among Males Recovering from Substance Abuse", Addictive Behaviors, 22(2):195-205, 1997.
Licinio et al., "The Hypothalamic-Pituitary-Adrenal Axis in Anorexia Nervosa", Psychiatry Research, 62:75-83, 1996.
Loose et al., "Ketoconazole Binds to Glucocotcoid Receptors and Exhibits Glucocorticoid Antagonist Activity in Cultured Cells", Journal of Clinical Investigations, 72:404-408, Jul. 1983.
Maher, "DNA Triple-Helix Formation: An Approach to Artificial Gene Repressors?", Bioassays, 14(12):807-815, 1992.
Mantsch et al., "Corticosterone Facilitates the Acquisition of Cocaine Self-Administration in Rats: Opposite Effects of the Type II Glucocorticoid Receptor Agonist Dexamethasone", Journal of Pharmacology and Experimental Therapeutics, 287(1):72-80, 1998.
Mantsch and Goeders, "Ketoconazole Blocks the Stress-Induced Reinstatement of Cocaine-Seeking Behavior in Rats: Relationship to the Discriminative Stimulus Effects of Cocaine", Psychopharmacology, 142:399-407, 1999.
Mantsch et al., "Corticosterone Facilitates the Acquisition of Cocaine Self-Administration in Rats: Opposite Effects of the Type II Glucocorticoide Receptor Agonist Dexamethasone", Journal of Pharmacology and Experimental Therapeutics, 287(1):72-80, 1998.
Mantsch and Goeders, "Effects of Cocaine Self-Administration on Plasma Corticosterone in Rats: Relationship to Hippocampal Type II Glucocorticoid Receptors", Progress in Neuro-Psychopharmacology and Biological Psychiatry, 24:633-646, 2000.
Mendelson et al., "Buprenorphine Attenuates the Effects of Cocaine on Adrenocorticotropin (ACTH) Secretion and Mood States in Man", Neuropsychopharmacology, 7(2):157-162, 1992.
Mendelson et al., "Effects of Low- and High-Nicotine Cigarette Smoking on Mood States and the HPA Axis in Men", Neuropsychopharmacology, 30:1751-1763, 2005.
Bech et al., "A case of sequential anti-stress medication in a patient with major depression resistant to amine-reuptake inhibitors." Acta Psychiatrica Scandinavica 100: 76-78, 1999.
Brown et al., "Ketoconazole inhibits Chlordiazepoxide (Cdx) Clearance in Man-Differences in Acute and Chronic Treatment." Hepatology, 4(5):1036-1036, 1984.
Lamberts et al., "Differential effects of the imidazole derivatives etomidate, ketoconazole and miconazole and of metyrapone on the secretion of cortisol and its precursors by human adrenocortical cells." Journal of Pharmacology and Experimental Therapeutics 240:259-264, 1987 (Abstract).
Kuipers et al., "Inhibition and induction of bile acid synthesis by ketoconazole, Effects on bile formation in the rat." Lipids 24:759-764,1989 (abstract).
Nagai et al., "Effect of ketoconazole, etomidate and other inhibitors of steroidogenesis on cytochrome P-450sccll-catalyzed reactions." Journal of Steroid Biochemistry 28:333-336, 1987 (Abstract).
Ohyama and Okuda, "Isolation and characterization of a cytochrome P-450 from rat kidney mitochondria that catalyzes the 24-hydroxylation of 25-hydroxyvitamin D3." Journal of Biological Chemistry 266:8690-8695, 1991.
International Preliminary Report on Patentability for PCT/US2006/044126 mailed May 15, 2008.
Extended European Search Report for European Application No. 12152933.3 dated Jul. 17, 2012.
International Preliminary Report on Patentability Chapter I for PCT/US2011/040647 mailed on Dec. 19, 2012.
International Search Report and Written Opinion for PCT/US2011/040647 mailed Mar. 2, 2012.
Supplementary European Search Report for European Application No. 11796418.9 dated Nov. 22, 2013.
Azizi et al., Aldosterone synthase inhibition in humans. Nephrol Dial Transplant. Jan. 2013;28(1):36-43. doi: 10.1093/ndt/gfs388. Epub Oct. 8, 2012.
Bertagna et al., LCI699, a potent 11β-hydroxylase inhibitor, normalizes urinary cortisol in patients with Cushing's disease: results from a multicenter, proof-of-concept study. J Clin Endocrinol Metab. Apr. 2014;99(4):1375-83. doi: 10.1210/jc.2013-2117. Epub Dec. 11, 2013.
De Lind Van Wijngaarden et al., High prevalence of central adrenal insufficiency in patients with Prader-Willi syndrome. J Clin Endocrinol Metab. May 2008;93(5):1649-54. doi: 10.1210/jc.2007-2294. Epub Feb. 26, 2008.
Drouet et al., Metyrapone blunts stress-induced hyperthermia and increased locomotor activity independently of glucocorticoids and neurosteroids. Psychoneuroendocrinology. Oct. 2010;35(9):1299-310. doi: 10.1016/j.psyneuen.2010.03.001. Epub Mar. 24, 2010.
Freel et al., Endogenous corticosteroid biosynthesis in subjects after bilateral adrenalectomy. Clin Endocrinol (Oxf). May 2007;66(5):659-65. Epub Mar. 23, 2007. Erratum in: Clin Endocrinol (Oxf). Jun. 2007;66(6):901. Bernhardt, M [corrected to Bernhardt, R]; Ingram, R [corrected to Ingram, M].

(56) References Cited

OTHER PUBLICATIONS

Goeders and Guerin, Effects of the combination of metyrapone and oxazepam on cocaine and food self-administration in rats. Pharmacol Biochem Behav. Nov. 2008;91(1):181-9. doi: 10.1016/j.pbb.2008.07.005. Epub Jul. 19, 2008.

Goeders et al. The combination of metyrapone and oxazepam reduces intravenous nicotine self-administration in rats. ACNP 49th annual meeting. Dec. 5-9, 2010.

Guerin and Goeders, Effects of metyrapol on cocaine self-administration in rats. Society for Neuroscience, annual meeting abstract. Nov. 18, 2008.

Ichimura, [Studies on the hypothalamo-pituitary adrenal axis in children by using 11-beta-hydroxylase inhibitors. I. A gas chromatograph-mass spectrometric method for the determination of serum metyrapone and reduced metyrapone; a pharmacokinetic and biological study of metyrapone in children]. Nihon Naibunpi Gakkai Zasshi. May 20, 1983;59(5):715-37. Japanese.

Keller et al., Combinations of oxazepam and metyrapone attenuate cocaine and methamphetamine cue reactivity. Drug Alcohol Depend. Dec. 1, 2013;133(2):405-12. doi: 10.1016/j.drugalcdep.2013.06.025. Epub Jul. 26, 2013.

Kreek et al., Pharmacotherapy of addictions. Nat Rev Drug Discov. Sep. 2002;1(9):710-26. Review. Erratum in: Nat Rev Drug Discov Nov. 2002;1(11):920.

Luchetti et al., Neurosteroid and GABA-A receptor alterations in Alzheimer's disease, Parkinson's disease and multiple sclerosis. Neuroscience. Sep. 15, 2011;191:6-21. doi: 10.1016/j.neuroscience.2011.04.010. Epub Apr. 15, 2011.

MacKenzie et al., Expression of 11beta-hydroxylase and aldosterone synthase genes in the rat brain. J Mol Endocrinol. Jun. 2000;24(3):321-8.

Mueller et al., Differential regulation of glucocorticoid synthesis in murine intestinal epithelial versus adrenocortical cell lines. Endocrinology. Mar. 2007;148(3):1445-53. Epub Dec. 14, 2006.

Parnham and Sneddon, The influence of metyrapone on the synthesis and release of prostaglandins from the pregnant rat uterus in vitro. Br J Pharmacol. Dec. 1975;55(4):535-9.

Raven et al., The relationship between the effects of metyrapone treatment on depressed mood and urinary steroid profiles. Psychoneuroendocrinology. Apr. 1996;21(3):277-86.

Reuter et al., The role of cortisol suppression on craving for and satisfaction from nicotine in high and low impulsive subjects. Hum Psychopharmacol. Jul. 2002;17(5):213-24.

Wright et al., Attenuating corticosterone levels on the day of memory assessment prevents chronic stress-induced impairments in spatial memory. Eur J Neurosci. 2006; 24:595-605.

Ye et al., Effects of ACTH, dexamethasone, and adrenalectomy on 11beta-hydroxylase (CYP11B1) and aldosterone synthase (CYP11B2) gene expression in the rat central nervous system. J Endocrinol. Feb. 2008;196(2):305-11. doi: 10.1677/JOE-07-0439.

U.S. Appl. No. 13/350,192, filed Jan. 13, 2012, Goeders.

U.S. Appl. No. 14/736,619, filed Jul. 11, 2015, Goeders et al.

PCT/US2006/044126, May 15, 2008, International Preliminary Report on Patentability.

EP 12152933.3, Jul. 17, 2012, European Search Report.

PCT/US2011/040647, Mar. 2, 2012, International Search Report and Written Opinion.

PCT/US2011/040647, Jan. 3, 2013, International Preliminary Report on Patentability.

EP 11796418.9, Nov. 22, 2013, Supplementary European Search Report.

\* cited by examiner

FIG. 14

| | Cocaine | SEM | Ecgonine Methyl ester | SEM | benzoylecgonine | SEM | oxazepam | SEM | metyrapone | SEM | metyrapol | SEM |
|---|---|---|---|---|---|---|---|---|---|---|---|---|
| VEH | 517 | 36 | 19 | 3 | 642 | 35 | 15 | 8 | 0 | 0 | 0 | 0 |
| OX 5 MET 25 | 529 | 50 | 35 | 3 | 694 | 58 | 864 | 182 | 2458 | 667 | 10383 | 1709 |
| OX 10 MET 25 | 713 | 131 | 11 | 3 | 516 | 78 | 1408 | 228 | 3351 | 464 | 10047 | 1307 |
| OS 10 MET 50 | 578 | 52 | 23 | 6 | 687 | 38 | 1509 | 281 | 5864 | 2040 | 18134 | 2661 |
| OX 30 MET 50 | 720 | 51 | 26 | 2 | 698 | 79 | 2321 | 690 | 6720 | 1218 | 17353 | 1032 |
| OX 40 MET 25 | 694 | 223 | 24 | 5 | 491 | 36 | 3259 | 773 | 2590 | 430 | 9482 | 1716 |

COMPOSITIONS AND METHODS FOR THE TREATMENT OF ADDICTION AND OTHER NEUROPSYCHIATRIC DISORDERS

RELATED APPLICATIONS

This application claims the benefit of U.S. Application No. 60/735,507, filed Nov. 10, 2005, and U.S. Application No. 60/764,727, filed Feb. 2, 2006. For the purpose of any U.S. patent that may issue from the present application, the contents of these two earlier-filed applications are hereby incorporated by reference herein in their entireties.

TECHNICAL FIELD

This invention relates to methods for treating a variety of conditions and disorders, including neuropsychiatric disorders such as addiction, anxiety, depression, schizophrenia, and related conditions (e.g., insomnia), and more generally to methods of making and using pharmaceutical formulations that target distinct tissues within the nervous and endocrine systems.

SUMMARY OF THE INVENTION

The present invention is based, in part, on our discovery that certain types of therapeutic agents can be used in combination to treat a variety of neuropsychiatric and related disorders, including addiction (e.g., an addiction to a substance such as a drug or to an activity such as gambling). More specifically, these agents can be used to treat eating disorders; depression; disruptive behavior disorders (e.g., attention deficit disorders such as attention deficit and hyperactivity disorder (ADHD)); schizophrenia; anxiety (e.g., anxiety experienced in the context of post-traumatic stress disorder); sleep disorders; and/or related or resulting conditions. For example, the invention includes compositions and methods that can be used to treat or prevent obesity or various eating disorders. The compositions can also be used in the treatment or prevention of insomnia, which can occur independently or in connection with conditions associated with stress or stress-related disorders (e.g., an anxiety). More generally, these conditions can be described as those associated with hypercortisolism, other activities within the hypothalamic-pituitary-adrenal (HPA) axis (e.g., altered regulation of adrenocorticotropic hormone (ACTH)) or prefrontal cortex, and/or excessive activity in the sympathetic nervous system.

The present compositions can also be used to alleviate some of the symptoms experienced during menopause or associated with the menstrual cycle (e.g., pre-menstrual syndrome (PMS)).

Accordingly, the invention features pharmaceutical compositions and methods by which they can be prepared and administered (e.g., prescribed and self-administered) to a patient. Given the current norms, we expect the therapeutic agents described herein will be formulated in a single preparation (e.g., a single tablet, capsule, or the like, which may be designed to produce a sustained and controlled release) and administered orally. The invention is not so limited, however, and exemplary alternatives for combining and administering the therapeutic agents are described further below (e.g., solutions can be administered intravenously).

Regardless of the precise formulation or configuration, the compositions can include at least one active ingredient that targets the hypothalamo-pituitary-adrenal (HPA) axis and at least one active ingredient that targets the prefrontal cortex (e.g., by targeting $GABA_A$ receptors in the prefrontal cortex). More specifically, the compositions can include at least one of a first active agent that: inhibits corticotropin-releasing hormone (CRH); inhibits adrenocorticotropic hormone (ACTH); and/or inhibits cortisol. For example, the agent can reduce the ability of CRH to stimulate the release of ACTH from the pituitary gland, reduce the ability of ACTH to stimulate the release of cortisol from the adrenal gland, or inhibit cortisol synthesis, secretion, or activity. For example, while the present compositions are not limited to those that exert their effect by any particular mechanism, agents that inhibit cortisol activity may do so by competing with cortisol for glucocorticoid receptor binding and/or blocking a downstream event such as receptor activation, dimerization or transcriptional signaling through a glucocorticoid response element. These agents may also be agents that bind to another type of adrenocorticosteroid receptor, such as a mineralocorticoid receptor, and/or that inhibit downstream events following mineralocorticoid receptor binding.

The compositions can further include at least one of a second active agent that targets the prefrontal cortex by, for example, increasing the expression or activity of gamma-aminobutyric acid (GABA); mimicking GABA; inhibiting GABA metabolism in the prefrontal cortex; and/or otherwise stimulating GABA signaling in the prefrontal cortex. As noted, the compositions can contain these first and second agents by virtue of a physical combination of the agents per se (e.g., in an admixture or suspension) in, for example, a sustained-release preparation. In other embodiments, the compositions can be combined by virtue of a shared packaging (e.g., tablets containing the first active agent and tablets containing the second active agent can be combined in a single blister pack, optionally marked to indicate days of the week and/or times of the day). Solutions for intravenous administration can similarly be packaged, with one solution containing the first agent and one solution containing the second agent, with instructions for simultaneous or sequential administration.

In specific embodiments, the compositions can include one or more of the types of agents listed in the first column of the following table and one or more of the types of agents listed in the second column.

| First active agent | Second active agent |
|---|---|
| An agent that inhibits CRH in the HPA axis or CNS, including the prefrontal cortex | An agent that directly or indirectly stimulates GABA in the prefrontal cortex |
| An agent that inhibits ACTH in the pituitary gland | An agent that mimics GABA in the prefrontal cortex |
| An agent that inhibits cortisol in the adrenal gland | An agent that inhibits GABA metabolism |

Either or both of these types of agents can be combined with an agent that inhibits activity in the sympathetic nervous system (e.g., a beta-blocker such as propranolol (Inderal®)). Beta-blockers and other agents (e.g., anxiolytics) that can be included as a "third" agent are described further below. Thus, the compositions or combination pharmacotherapies can include an agent that inhibits a beta-adrenergic receptor (e.g., by binding the receptor and inhibiting its interaction with epinephrine) or that otherwise act as anti-hypertensives or anxiolytic agents.

In specific embodiments, an agent that inhibits CRH can be combined with an agent that stimulates GABA in the prefrontal cortex and an agent that inhibits activity in the sympathetic nervous system; an agent that inhibits ACTH can be combined with an agent that stimulates GABA in the prefrontal cortex and an agent that inhibits activity in the sympathetic nervous system; an agent that inhibits cortisol can be combined with an agent that stimulates GABA in the prefrontal cortex and an agent that inhibits activity in the sympathetic nervous system; and one or more agents that bind to adrenocorticosteroid receptors can be combined with an agent that inhibits activity in the sympathetic nervous system. In any of these exemplary embodiments, the referenced agent can be one described herein (e.g., an agent that stimulates GABA can be an agent that directly or indirectly stimulates GABA in the prefrontal cortex; an agent that mimics GABA in the prefrontal cortex (e.g., a GABA receptor (e.g., $GABA_A$) agonist); or an agent that inhibits GABA metabolism).

GABA is an inhibitory neurotransmitter that hyperpolarizes the inhibited neuron following receptor binding. This binding opens chloride and potassium channels, either directly or indirectly. Activated ionotropic receptors are ion channels themselves while the metabotropic receptors are G protein-coupled receptors that activate ion channels via the intermediary G proteins. Either type of receptor can be activated by an agent serving to mimic GABA and thereby target the prefrontal cortex; Other agents can act by increasing GABA synthesis. For example, nucleic acids encoding the synthetic enzyme L-glutamic acid decarboxylase, or a biologically active fragment or other mutant thereof, can be administered to a patient who is likely to benefit from the methods described herein (e.g., a patient who has demonstrated or who has been diagnosed as having an addiction (other patients amenable to treatment are described elsewhere herein))

In other embodiments, the therapeutic composition can be a combination of at least two or three of (e.g., two, three, or four of): an agent that inhibits CRH, an agent that inhibits ACTH, an agent that inhibits cortisol (or binds an adrenocorticoid receptor), an agent that directly or indirectly stimulates GABA in the prefrontal cortex, an agent that mimics GABA in the prefrontal cortex, or an agent that inhibits GABA metabolism and an agent that inhibits activity in the sympathetic nervous system.

Unless the context indicates otherwise, we use the term "agent" to broadly refer to any substance that affects a target molecule (e.g., a ligand or the receptor to which it binds) or a target region of the brain or endocrine system in a clinically beneficial way (e.g., to inhibit HPA axis activation following a patient's exposure to one or more conditioned environmental cues). For example, we may refer to chemical compounds such as metyrapone (Metopirone®) as "agents". We may also use the term "compound" to refer to conventional chemical compounds (e.g., small organic or inorganic molecules). The "agent" may also be a protein or protein-based molecule, such as a mutant ligand or antibody. Other useful agents include nucleic acids or nucleic acid-based entities such as antisense oligonucleotides or RNA molecules that mediate RNAi and the vectors used for their delivery. For example, we may refer to an antibody that specifically binds and alters (e.g., inhibits) the activity of CRH (e.g., a human or humanized anti-CRH antibody) or to a nucleic acid (e.g., an siRNA or shRNA) that specifically interacts with, and inhibits translation of, an RNA encoding CRH as an "agent" that inhibits CRH. CRH is only one of the molecules that can be targeted; ACTH, cortisol, and GABA can be targeted by any of the types of agents discussed herein in reference to CHR. Compounds useful in the invention include those that bind a cortisol receptor. Preliminary results indicate that corticosterone is elevated in an animal model of addiction.

While agents useful in the compositions of the invention are described further below, we note here that agents that can inhibit CRH in the HPA include agents (e.g., nucleic acids) that inhibit CRH expression; agents that inhibit CRH production or secretion by way of participation in a negative feedback loop; antibodies that specifically bind to and inhibit CRH; CRH receptor antagonists (e.g., proteins, including antibodies, that bind the CRH receptor and inhibit signal transduction or that act intracellularly to inhibit the second messengers normally generated in response to CRH receptor binding); chemical compounds (e.g., small molecules) that inhibit the expression, secretion, or activity of CRH or the CRH receptor (e.g., compounds that inhibit the ability of CRH to bind cognate receptors in the pituitary); and agents that facilitate CRH metabolism. As noted, other agents can inhibit ACTH. For example, the compositions of the invention can include agents (e.g., nucleic acids) that inhibit ACTH expression; agents that inhibit ACTH production or secretion by way of participation in a negative feedback loop; antibodies that specifically bind to and inhibit ACTH; ACTH receptor antagonists (e.g., proteins that bind the ACTH receptor and inhibit signal transduction or that act intracellularly to inhibit the second messengers normally generated in response to ACTH receptor binding); chemical compounds that inhibit the expression, secretion, or activity of ACTH or the ACTH receptor (e.g., compounds that inhibit the ability of ACTH to bind cognate receptors in the adrenal gland); and agents that facilitate ACTH metabolism.

Agents that inhibit CRH include [Met18, Lys23, Glu27,29, 40, Ala32,41, Leu33,36,38] CRF9-41, which is abbreviated as alpha-helical CRF(9-41) and has the sequence Asp-Leu-Thr-Phe-His-Leu-Leu-Arg-Glu-Met-Leu-Glu-Met-Ala-Lys-Ala-Glu-Gln-Glu-Ala-Glu-Gln-Ala-Ala-Leu-Asn-Arg-Leu-Leu-Leu-Glu-Glu-Ala (SEQ ID NO: 1)) and biologically active fragments or variants thereof (Rivier et al., *Science* 224:889, 1984). Another agent that inhibits CRH is [D-Phe12, Nle21,38, (αMeLeu37)] CRF(12-41), which is abbreviated as D-Phe CRF12-41, and biologically active fragments and variants thereof. Other agents that inhibit CRH include Astressin®; CP-154,526; NB127914, Antalarmin®; CRA1000; CRA1001, and Antisauvagine-30. See also U.S. Pat. Nos. 6,326,463; 6,323,312; 4,594,329, and 4,605,642. It is known in the art that deleting certain N-terminal amino acid residues from CRF produces CRF antagonists, and these antagonists (e.g., CRF(8-41), CRF(9-41), and CRF(10-41)) can be used in the present compositions and methods. Cyclic peptides that inhibit CRF are described in U.S. Pat. No. 6,323, 312 and can be used in the present compositions and methods.

To inhibit ACTH, one can administer a sufficient amount of ACTH to inhibit ACTH through feedback inhibition or to down-regulate the ACTH receptor.

Chemical compounds that inhibit cortisol include metyrapone, ketoconazole, and aminoglutethamide. Useful compounds and other agents, including those described with particularity herein and/or otherwise known in the art, can act at any point along the HPA axis to down-regulate the effect of cortisol (i.e., they can act on the target (e.g., cortisol) directly (e.g., by binding to and inhibiting the target) or indirectly (e.g., by inhibiting a molecule active upstream from the target in the HPA axis)).

Substance P antagonists and vasopressin inhibitors can also be used in the present compositions and methods to inhibit activity within the HPA axis. Substance P is an 11-amino acid neuropeptide that binds a neurokinin 1 receptor. Antagonists include Aprepitant), which is currently available for chemotherapy-induced nausea, and MK-0869, which is an antidepressant and substance P receptor antagonist. [D-Arg$^1$,D-Pro$^2$,D-Trp$^{7,9}$,Leu$^{11}$]SP has been administered intravenously as a substance P antagonist.

Agents that augment endocannabinoid signaling can also be used to inhibit activity in the HPA axis and are useful in the present compositions and methods. These agents may stimulate the expression or activity of an endocannabinoid or may, for example, be or mimic an endocannabinoid (see Patel et al., *Endocrinol.* 145:5431-5438, 2004). While the invention is not limited to agents that exert their positive effect on the disorders and other conditions described herein by any particular mechanism, we note that endocannabinoids can inhibit the release of vasopressin from the posterior pituitary (Tasker, *Endocrinol.* 145:5429-5430, 2004). 29-5430. Exogenous cannabinoids have been shown to stimulate the HPA, but at least one such compound, CP55940, can instead reduce the stress-induced secretion of HPA hormones (Thomas et al., *J. Pharmacol. Exp. Ther.* 285:285-292, 1998).

An agent that directly or indirectly stimulates GABA in the prefrontal cortex may do so by directly or indirectly increasing the synthesis, release, or activity of GABA. Activity can be enhanced, for example, by enhancing the interaction between GABA and a cognate receptor. There are various ways to enhance this interaction, including increasing the concentration of GABA, providing a receptor agonist, or altering the kinetics of receptor binding and signal transduction. GABA concentration can, in turn, be increased by increasing GABA synthesis or inhibiting GABA metabolism. GABA concentrations are, in effect, also increased by the administration of agents that mimic GABA. With respect to indirect stimulation, any agent (e.g., an antidepressant) that preferentially increases dopaminergic or noradrenergic activity in the prefrontal cortex can indirectly affect (i.e., stimulate) GABA in the prefrontal cortex. Mirtazapine is an example of an antidepressant agent that could be used to indirectly stimulate GABA; atomoxetine is an example of another type of agent that can be similarly used. Gabapentin (Neurontin™) is an example of an agent that mimics the effect of GABA, and direct stimulators include any benzodiazepine (e.g., oxazepam ((Serax®) or chlordiazepoxide) or alprazolam (Xanax®). Other useful agents such as muscimol and baclofen may stimulate GABA through the $GABA_A$ or $GABA_B$ receptor, respectively. Other GABA agonists or mimics include progabide, riluzole, baclofen, vigabatrin, valproic acid (Depakote™), tiagabine (Gabitril™), lamotrigine (Lamictal™), phenytoin (Dilantin™), carbamazepine (Tegretol™) and topiramate (Topamax™).

While dosages are described further below, we note here that, when agents used within the compositions of the invention are ones that are presently known and used to treat patients, the dosage of at least one of the agents required in the context of our combination therapy may be less than the dosage at which that agent is currently and typically prescribed. For example, where the present compositions include a benzodiazepine that is currently used in the treatment of anxiety, the amount of that compound administered to a patient for the treatment of addiction can be less than a physician would have typically prescribed for the treatment of anxiety. In some instances, the dosages of both of the agents within the present compositions will be less than the traditional dosages of those agents. While the compositions of the invention are not limited to those that have particular advantages, we believe the ability to use low-dose formulations will reduce the incidence of side effects as well as the abuse potential associated with some of the agents. It is understood in the art that some patients may be more or less sensitive to a particular dosage of a given medication. In the present case, as is generally true, patients and their health care providers can monitor treatment for a desired effect and dosages may be variously adjusted (e.g., over time).

The amounts of chemical compounds within the present compositions can vary. For example, a patient may receive from about 1-1000 mg of a given first agent and 1-1000 mg of a given second agent at defined intervals. Where a third agent is included, the formulation can include and the patient may receive from 1-1000 mg of the third agent. For example, the patient can be treated every so-many hours (e.g., about every 2, 4, 6, 8, 12, or 24 hours), every so-many days (e.g., once a day, once every other day, once every three days), or every so-many weeks (e.g., once a week). For example, a patient may receive at least or about 5-1500 mg (e.g., at least or about 5, 10, 25, 50, 100, 200, 250, 300, 400, 450, 500, 550, 600, 650, 700, 750, 800, 850, 900, 1000, 1250, or 1500 mg)) of a first agent and at least or about 5-500 mg (e.g., at least or about 1, 5, 10, 20, 25, 30, 35, 40, 45, 50, 100, 200, 250, 300, 400, 450, 500) of a second agent from 1-4 times per day. Under such a regime, a patient could receive at least or about 10-6000 mg of a first agent (e.g., at least or about 25-1500 mg; 50-1250 mg; 100-1250 mg; 100-1000 mg; 250-1000 mg; 500-1000 mg; 750-1000 mg (e.g., about 750 mg or about 1000 mg)) such as metyrapone or ketoconazole. Under either the same or a different regime, a patient could receive about 5-100 mg of a second agent (e.g., about 5-50 mg; about 5-40 mg; about 5-30 mg; about 5-20 mg; about 5-10 mg; about 10-50 mg; about 10-40 mg; about 10-30 mg; about 20-50 mg; about 20-40 mg; about 20-30 mg; about 30-50 mg; or about 30-40 mg of a first agent). As noted, the second agent can be a benzodiazepine, such as oxazepam. As noted, appropriate dosages can be delivered over time from a sustained-release formulation, which may be administered at daily or weekly intervals. Where particular formulations or devices are used (e.g., an infusion pump), administration may proceed without the need for patient intervention for longer periods of time.

The amounts of the agents within a pharmaceutical preparation may be the same or different (e.g., the ratio of the first agent to the second can be at least or about 100:1; 90:1; 80:1; 75:1; 70:1; 65:1; 60:1; 55:1; 50:1; 45:1; 40:1; 35:1; 30:1; 25:1; 20:1; 15:1; 10:1; 9:1; 8:1; 7:1; 6:1; 5:1; 4:1; 3:1; 2:1; or about 1:1). For example, a composition can contain about 1 equivalent of oxazepam to about 25-50 equivalents of metyrapone; about 25-50 equivalents of ketoconazole to about 1 equivalent of alprazolam; about 25-50 equivalents of ketoconazole to about 1 equivalent of oxazepam; about 25-50 equivalent of metyrapone to about 1 equivalent of alprazolam; about 1 equivalent of muscimol to about 25-50 equivalents of CP-154,526; or about 1 equivalent of muscimol to about 25-50 equivalents of metyrapone. An equivalent can be a unit of weight (e.g., a milligram). The ratios can run differently, however, with the amount of the second agent exceeding the amount of the first agent (by, for example, the varying extent described here). The relative amounts of the active ingredients can also be expressed in terms of percentage. For example, relative to one another, the amount of the second agent can be at least or about 1-99% of the amount of the second agent. Where a third agent is included to inhibit the sympathetic nervous system, the relative amount of that agent can also vary with respect to the first and second agents. For example, relative to one another, the amount of the third agent can be at least or about 1-99% of the amount of the first or second agent. Where the third agent is included in a composition and/or used in a treatment regime, it may allow use of either the first and/or the second agent in an amount that is lower than predicted or that is required for efficacy in the absence of the third agent.

The pharmaceutical compositions, which are described further below, can include standard ingredients such as carriers and preservatives. The compositions can also include substances (e.g., a polyethylene glycol) to increase the solubility of the active ingredients. Typically, the active ingredients will account for a minority of the overall composition. For example, the first, second, and/or third agents can constitute about 1-50% of the pharmaceutical composition (e.g., about 1-40%; 1-30%; 1-20%; 1-10%; 2-40%; 2-30%; 2-20%; 2-10%; 2-5%; 3-40%; 3-30%; 3-20%; 3-10%; 3-5%; 4-40%; 4-30%; 4-20%; 4-10%; 4-5%; 1-2%; 1-3%; 1-4%; 2-4%; 2-3%; or 3-4% of the pharmaceutical composition).

When an agent "targets" an area within a patient's nervous system or endocrine system, it affects the activity of cells within that area in such a way as to confer a benefit on the patient. For example, where a patient is addicted to a substance or activity, the benefit can be a reduction in the patient's engagement with that substance or activity. For example, the patient may use the substance or carry out the activity less frequently or to a lesser extent than one would expect in the absence of treatment or to a lesser extent than prior to treatment. Thus, the benefit can be characterized as a reduction in the risk of relapse, even in the presence of conditioned environmental cues. The clinical benefit can be subjective in that patients may report a reduction in their craving for a substance or activity. Thus, the compounds and methods of the invention can be used to promote abstinence or periods of abstinence that are longer than one would expect in the absence of treatment. Achieving any detectable improvement constitutes "treatment" of an addiction with the present compositions and methods; complete recovery may be achieved, but is not required to constitute treatment. The same is true regarding other indications. For example, a detectable improvement in the event of an anxiety-associated disorder, an eating disorder, a sleeping disorder, schizophrenia, or an unpleasant symptom of menopause constitutes treatment. Complete absence of any difficulty is not required.

While we believe we understand certain events that occur in the course of treatment, the compositions of the present invention are not limited to those that work by affecting any particular cellular mechanism. Our working hypothesis is that, with respect to addiction, the cues that trigger relapse to undesirable behaviors (e.g., addictive behaviors) produce those behaviors (or desires to behave) through a conditioned activation of the HPA axis that affects neuronal activity in the prefrontal cortex. More specifically, the conditioned activation of the HPA axis increases the secretion of corticotropin-releasing hormone (CRH), adrenocorticotropic hormone (ACTH) and cortisol (corticosterone in rats) and these hormones, in turn, affect activity in the prefrontal cortex (the medial prefrontal cortex in rats), a brain region involved in reward, judgment and other activities related to a propensity to relapse. When administered to treat an addiction, we believe the combination therapies described herein reduce the likelihood of relapse by decreasing activity within the HPA axis and/or the prefrontal cortex. This reduces the cue-induced secretion of CRH, ACTH, and/or cortisol to levels too low to evoke the cravings associated with addiction to a substance or undesirable behavior. As these hormones (CRH, ACTH, and cortisol) affect activity in the prefrontal cortex, we expect prefrontal activity to subsequently decline as well, and the second agent of the composition(s) can facilitate that decline.

As noted, the active ingredients of the present compositions can be combined in a single formulation or by virtue of their packaging. Accordingly, the present invention features kits containing single formulations and/or dual-packaged formulations together with instructions for their use. For example, the compositions can either be combined within a single tablet or capsule or divided between tablets and placed within a blister pack optionally marked to indicate the day or time of day it should be taken.

As noted, the compositions can be used to treat addiction to a variety of compounds (i.e., to treat substance abuse) or activities. For example, the compositions can be used to treat addiction to stimulants (e.g., cocaine, amphetamines, methamphetamines, methylphenidate, and related stimulants), opiates (e.g., heroin, codeine, hydrocodone, and related opioid drugs), nicotine, alcohol, prescription medications (e.g., medications prescribed for pain management such as Percodan® or Percocet®), and naturally-occurring plant-derived drugs (e.g. marijuana, tobacco, and the addictive agents therein). Patients being treated with methadone are also candidates for treatment with the compositions described herein. The present compositions may help such patients step-down and discontinue use of methadone. Patients who engage in addictive behaviors can also be identified and treated. These patients may be suffering from an addiction to gambling, sex, or food. In each of these disorders, conditioned cues are believed to induce or contribute to relapse.

Alternatively, or in addition, the compositions described herein can be used to treat other neuropsychiatric disorders that involve HPA axis activity and the prefrontal cortex. These include anxiety, including but not limited to anxiety associated with panic disorder, obsessive compulsive disorder (OCD), post-traumatic stress disorder (PTSD), social anxiety disorder, generalized anxiety disorder, and obesity. Patients diagnosed as suffering from depression can also be treated. Their depression can be, but is not necessarily, associated with major depressive disorder, dysthymia, bipolar depression, depression associated with medical conditions, and depression associated with substance abuse.

Other conditions amenable to treatment are obesity and various eating disorders, including Prader Willi Syndrome. Other patients amenable to treatment include those suffering from schizophrenia; those with disruptive behavior disorders (e.g., attention-deficit disorder (ADD) or ADHD); those experiencing menopause; and those suffering from a menstrual cycle-related syndrome (e.g., PMS). Other conditions amenable to treatment are insomnia and various sleep disorders.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 14 is a table summarizing the test conditions and results of a pharmacokinetic analysis of cocaine, metyrapone, and oxazepam.

DETAILED DESCRIPTION

Figure 1A:
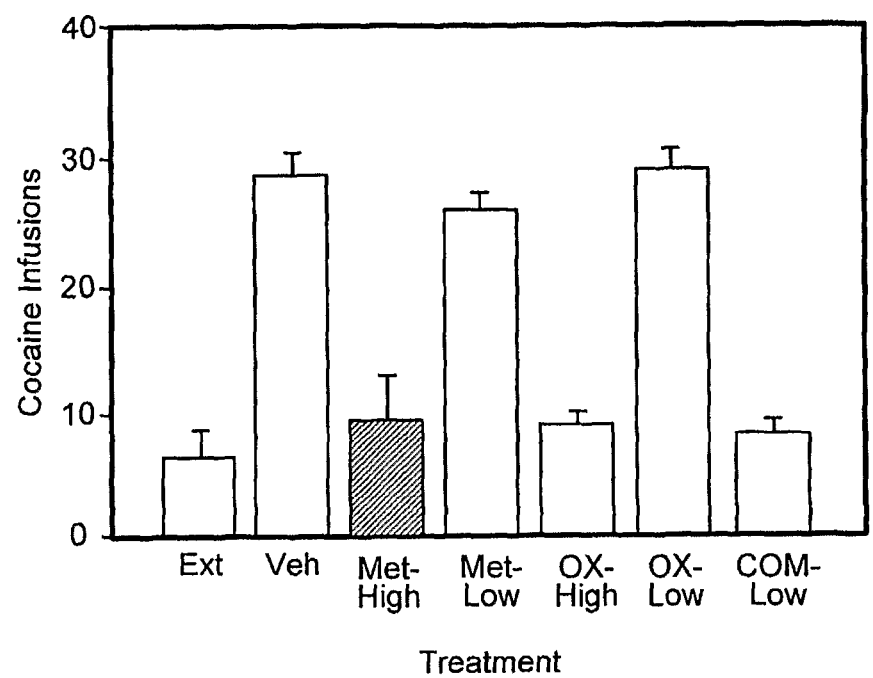
FIGS. 1A and 1B are bar graphs illustrating the effect of the combination of metyrapone and oxazepam on intravenous cocaine self-administration in rats. The number of cocaine infusions is plotted in FIG. 1A, and the number of infusions expressed as a percentage of the baseline is plotted in FIG. 1B.

The compositions described herein include two or more therapeutic agents for the treatment of addiction, other neuropsychiatric disorders, and independent or associated conditions. One or more of the agents included in the formulations can be an agent that is currently available but not currently prescribed for the indication(s) described herein. For example, metyrapone is commonly used to diagnose malfunction of the adrenal glands, and oxazepam is a benzodiazepine used to treat anxiety and related disorders. Both of these drugs affect physiological systems related to stress and the subsequent activation of the HPA axis. Alternatively, one or more of the agents can be newly formed in accordance with the teachings herein. For example, an antisense oligonucleotide or an RNA molecule that mediates RNAi can be produced given the sequence(s) of the target(s) discovered (i.e., CRH, ACTH, a GABA receptor (e.g., $GABA_A$ or a component of the $GABA_A$ receptor complex, as can be targeted by any of the "second" agents described herein) or β adrenergic receptors in the sympathetic nervous system. The sequences of these targets are known or readily available to one of ordinary skill in the art, as are methods for making antisense oligonucleotides and RNA molecules that mediate RNAi. Other useful agents, whether previously available or newly made, include antibodies that specifically bind a ligand identified herein (e.g., CRH, ACTH, or GABA) or a receptor activated in response to conditioned environmental cues (e.g., a receptor for CRH, ACTH, cortisol, or GABA). Where an agent is employed to inhibit activity in the sympathetic nervous system, it may be a chemical compound, such as those provided herein, or another type of agent. For example, one can administer nucleic acids or nucleic acid-based agents to inhibit the expression of β adrenergic receptors or antibodies that specifically bind and antagonize these receptors. Upon specific binding, the antibody can act as an agonist or antagonist of the entity bound, as desired to facilitate or inhibit cellular activity mediated by receptor binding. For example, an antibody that specifically binds CRH can act as a CRH antagonist; an antibody that specifically binds a GABA receptor can act as a GABA receptor agonist; an antibody that specifically binds a β adrenergic receptor can act as an adrenaline antagonist; an antibody that specifically binds a glucocorticoid receptor can act as an antagonist to inhibit cortisol; and so forth.

Work conducted in our laboratory has demonstrated that the HPA axis plays an important role in drug addiction (Goeders, *Psychoneuroendocrinology* 22:237, 1997; Goeders, *J. Pharmacol. Exp. Ther.* 301:785-789, 2002; Goeders, *Psychoneuroendocrinology* 27:13-33, 2002; Goeders, *Eur. Neuropsychopharmacology* 3:435-441, 2003), and we now have data indicating that certain combinations of drugs (e.g., the combination of metyrapone and oxazepam) are effective in treating addiction (as evidenced by reducing cocaine reward). Accordingly, the invention features compositions that represent combined therapeutic agents (e.g., combinations of two or three agents that target the regions of the nervous and/or endocrine systems (e.g., the HPA axis and the sympathetic nervous system) described herein) and methods of treating patients with these agents (e.g., with a "first" and "second" agent or a "first" and "third" agent, as described herein).

Regardless of the substance or activity to which a patient is addicted, the extent of the addiction can vary; it may, to a greater or lesser extent impact the patient's ability to participate in or cope with life's daily events, and it may recur with varying frequency (e.g., the patient may experience a rare relapse or a fairly regular and/or frequent relapse).

The agents can be categorized in various ways, and the compositions of the invention can include two or more agents of the same or different types. For example, the agents can be categorized as chemical compounds (e.g., metyrapone and topiramate); as protein or protein-based molecules, such as mutant ligands (e.g., a ligand that binds but does not activate or fully activate its cognate receptor) as antibodies; or as nucleic acids or nucleic acid-based entities, such as antisense oligonucleotides or RNA molecules that mediate RNAi. Thus, the compositions of the invention can include two or more chemical compounds; two or more distinct protein or protein-based molecules; or two or more distinct nucleic acids or nucleic acid-based entities. Alternatively, the compositions can include two different types of agents (e.g., a protein and a nucleic acid or a chemical compound and a protein such as an antibody or an active fragment thereof). The methods by which patients are treated can similarly include administration of two or more chemical compounds; two or more distinct proteins or protein-based molecules; two or more distinct nucleic acids or nucleic acid-based entities; or any combination of agents of these various types (e.g., a protein and a nucleic acid).

Either or both of the agent(s) that target(s) the HPA axis and the agent(s) that target(s) the prefrontal cortex can be combined with an agent that inhibits activity in the sympathetic nervous system. Either or both of these types of agents can be combined with a beta blocker, suitable examples of which are provided below, or another type of antihypertensive and/or anxiolytic agent (e.g., an angiotensin II inhibitor such as candasartan). The third agent (i.e., the agent used in addition to the agent that targets the HPA axis and/or the agent that targets the prefrontal cortex) can also be an antidepressant, including any of the agents in the SSRI (selective serotonin reuptake inhibitor) class.

Useful Chemical Compounds:

Agents useful in targeting the HPA axis include metyrapone and ketoconazole. Metyrapone inhibits corticosterone synthesis by inhibiting the 11β-hydroxylation step in the synthesis of adrenocorticosteroids (Sonino, In: Agarwal (Ed), Hormone antagonists, Walter de Gruyter, Berlin, pp 421-429, 1982; Haleem et al., *Brain Res.* 458, 339-347, 1988; Haynes, In: Gilman et al. (Eds), The Pharmacological Basis of Therapeutics, eighth edition, Pergamon Press, New York, pp. 1431-1462, 1990).

Figure 13:
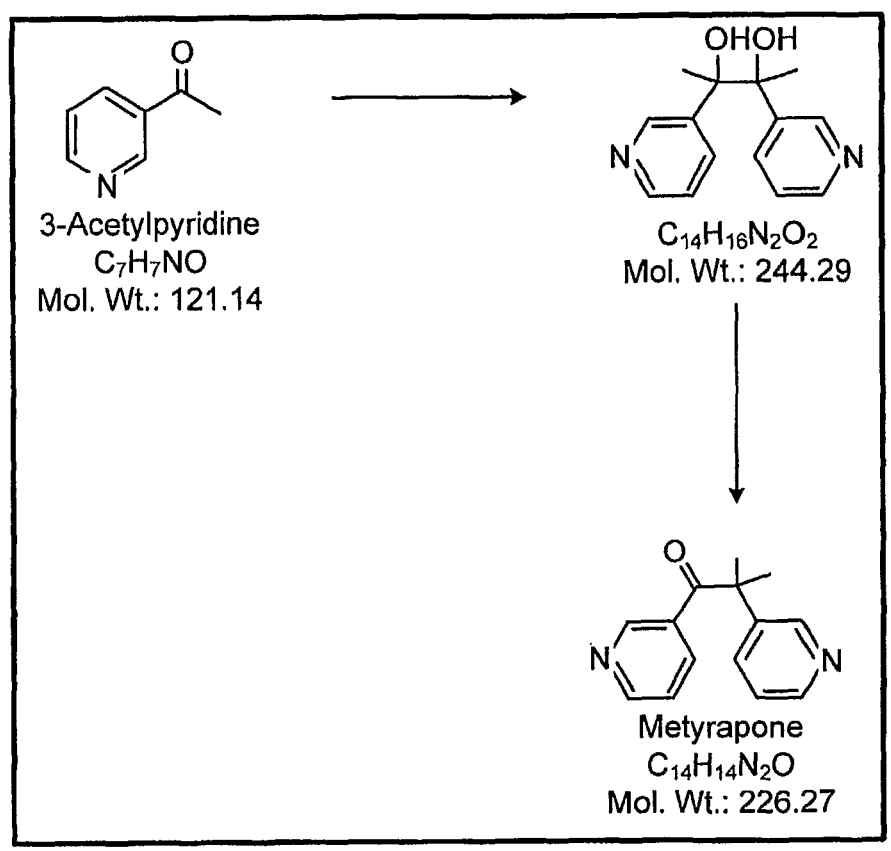
FIG. 13 is a schematic representing a synthetic pathway for synthesis of metyrapone.

Metyrapone is commercially available and can be synthesized by contract manufacturers (e.g., a pharmaceutical services company). In one scheme, metyrapone can be synthesized in a two-step process in which a starting material is exposed to ultraviolet light (see, e.g., the synthetic pathway illustrated in FIG. 13).

The effect of metyrapone administration can be assessed by measuring plasma concentrations of cortitosterone. We investigated the effects of the corticosterone synthesis inhibitor metyrapone and ketoconazole on cocaine self-administration (see below). Pretreatment with metyrapone resulted in significant dose-related decreases in both plasma corticosterone and ongoing cocaine self-administration, suggesting that corticosterone is involved in cocaine reward (see also Goeders et al., *Brain Res.* 722:145-152, 1996).

Ketoconazole is an oral antimycotic agent with a broad spectrum of activity and low toxicity that is used in the treatment of fungal disease (Sonino, In: Agarwal (Ed), Hormone Antagonists, Walter de Gruyter, Berlin, pp 421-429, 1982; Thienpont et al., *Experientia* 35:606-607, 1979). This drug also inhibits the 11β-hydroxylation and 18-hydroxylation steps in the synthesis of adrenocorticosteroids (Engelhardt et al., *Klin. Wochenschr.* 63:607-612, 1985) and may also function as a glucocorticoid receptor antagonist (Loose et al., *J. Clin. Invest.* 72:404-408, 1983). Furthermore, clinical trials have suggested that ketoconazole (as well as metyrapone) is effective in the treatment of hypercortisolemic depression that is resistant to standard antidepressant therapy (Ghadirian et al, *Biol. Psychiatry* 37:369-375, 1995; Murphy et al., *J. Clin. Psychopharmacol.* 11:121-126, 1991; Wolkowitz et al., *Am. J. Psychiatry* 150:810-812, 1993).

Agents that inhibit CRH include [Met18, Lys23, Glu27,29, 40, Ala32,41, Leu33,36,38] CRF9-41, which is abbreviated as alpha-helical CRF(9-41) and has the sequence Asp-Leu-Thr-Phe-His-Leu-Leu-Arg-Glu-Met-Leu-Glu-Met-Ala-Lys-Ala-Glu-Gln-Glu-Ala-Glu-Gln-Ala-Ala-Leu-Asn-Arg-Leu-Leu-Leu-Glu-Glu-Ala (SEQ ID NO:1)) and biologically active fragments or variants thereof (Rivier et al., *Science* 224:889, 1984). Another agent that inhibits CRH is [D-Phe12, Nle21,38, (αMeLeu37)] CRF(12-41), which is abbreviated as D-Phe CRF12-41, and biologically active fragments and variants thereof. Other agents that inhibit CRH include Astressin®; CP-154,526; NB127914, Antalarmin®; CRA1000; CRA1001, and Antisauvagine-30. See also U.S. Pat. Nos. 6,326,463; 6,323,312; and 4,594,329.

To inhibit ACTH, one can administer a sufficient amount of ACTH to inhibit ACTH through feedback inhibition or to down-regulate the ACTH receptor. Compounds can be tested for their ability to affect ACTH in various assays, including cell culture assays using, for example, rat anterior pituitary cells in monolayer culture (see *Endocrinol.* 91:562, 1972).

Agents that inhibit activity within the HPA axis also include substance P antagonists (e.g., [D-Arg1,D-Pro2,D-Trp7,9,Leu11]SP) and vasopressin antagonists.

As noted, in addition to metyrapone, ketoconazole, or another agent that inhibits the HPA axis, the therapeutic agents of the present invention can include one or more agents that target the prefrontal cortex by targeting GABA. Benzodiazepines (e.g., oxazepam) are one class of drugs useful in that regard. Benzodiazepines are among the most widely prescribed drugs for the pharmacological management of anxiety (Baldessarini, In: Hardman et al. (Eds), Goodman & Gilman's The Pharmacological Basis of Therapeutics, McGraw-Hill, New York, pp. 399-430, 1996). As some of the major symptoms associated with cocaine withdrawal often include severe anxiety, restlessness and agitation (Crowley, In: Fisher et al. (Eds), Cocaine: Clinical and Biobehavioral Aspects, Oxford University Press, New York, pp. 193-211, 1987; Gawin and Ellinwood, *Ann. Rev. Med.* 40:149-161, 1989; Tarr and Macklin, *Pediatric Clinics of North America* 34:319-331, 1987), benzodiazepines may be useful for alleviating these negative symptoms during the early stages of withdrawal, and a benzodiazepine incorporated in the combination therapies described herein can be used to treat patients who exhibit these and similar symptoms (i.e., anxiety, restlessness and agitation), whether in the context of an addiction or in connection with another event (e.g., another neuropsychiatric event, menopause, or PMS). These drugs are also useful in the emergency room for the treatment of some of the medical complications associated with cocaine intoxication since convulsions are often apparent following an acute overdose. These seizures can be effectively treated with intravenous diazepam (Valium®) (Gay, *J. Psychoactive Drugs* 13:297-318, 1981; Tarr and Macklin, *Pediatric Clinics of North America* 34:319-331, 1987), and diazepam can be used in the combination therapies described herein. Benzodiazepine receptor expression can be assessed using methods known in the art. For example, receptors can be labeled with [$^3$H]PK11195 (see Javaid et al., *Biol. Psychiatry* 36:44-50, 1994; see also Chesley et al., *J. Clin. Psychiatry* 51:404-406, 1990). The data described below further suggests that benzodiazepines mediate certain aspects of cocaine reinforcement in rats.

Useful benzodiazepines or agents that target the prefrontal cortex include oxazepam, as noted above, as well as chlordiazepoxide, mirtazapine, atomoxetine, gabapentin (Neurontin™), muscimol, progabide, riluzole, baclofen, vigabatrin, valproic acid (Depakote™), tiagabine (Gabitril™), lamotrigine (Lamictal™), phenytoin (Dilantin™), carbamazepine (Tegretol™), and topiramate (Toparnax™).

Other useful benzodiazepines include lorazepam (Ativan®), prazepam (Centrax®), flurazepam (Dalmane®), clonazepam (Klonopin®), chlordiazepoxide (Librium®), halazepam (Paxipam®), temezepam (Restoril®), clorazapate (Tranxene®), diazepam (Valium®), and alprazolam (Xanax®).

Where an agent that inhibits activity in the sympathetic nervous system is included, that agent can be a beta blocker or another type of antihypertensive agent. More specifically, the agent can be sotalol (Betapace®), imolol (Blocadren®), carteolol (Cartrol®), carvedilol (Coreg®), nadolol (Corgard®), nadol/bendroflunetazide (Corzide®), propranolol (Inderal®), propranolol/HCTZ (Inderide®), betaxolol (Kerlone®), penbutolol (Levatol®), metoprolol (Lopressor®), labetalol (Normodyne®), acebutolol (Sectral®), atenolol/HCTZ (Tenoretic®), atenolol (Tenormin®), timolol/HCTZ (Timolide®), metoprolol (Toprol®), labetalol (Trandate®), pindolol (Visken®), bisoprolol (Zebeta®), bisoprolol/HCTZ (Ziac®), esmolol (Brevibloc®), or combinations thereof.

Alternatively, or in addition, where an agent that inhibits activity in the sympathetic nervous system is included, it can be an SSRI. Currently available SSRIs, any of which or any combination of which can be used in the present compositions and methods, include citalopram (Celexa®), escitalopram oxalate (Lexapro®), fluvoxamine (Luvox®), paroxetine (Paxil®), fluoxetine (Prozac®), and sertraline (Zoloft®).

Other useful agents that target the sympathetic nervous system, and which may be categorized as anxiolytic agents, are angiotensin II inhibitors, and these agents include candasartan (Atacand®), eprosartan (Teveten®), irbesartan (Avapro®), losartan (Cozaar®), telmisartan (Micardis®), or valsartan (Diovan®).

Benzodiazepines are anxiolytic agents, and they may be incorporated in the present compositions as either an agent that targets the prefrontal cortex and/or as an agent that inhibits the sympathetic nervous system.

The invention features pharmaceutically acceptable salts, solvates, or hydrates of any of the present compounds (i.e., of any of the compounds suggested herein, generally or specifically, for use in combination), and prodrugs, metabolites, structural analogs, polymorphs, and other pharmaceutically useful variants thereof, whether present as crystals, milled and stabilized as nanocrystals, or in a non-crystalline form. These other variants may be, for example, complexes containing the compound (e.g., metyrapone) and a targeting moiety, as described further below, or a detectable marker (e.g., the compound may be joined to a fluorescent compound or may incorporate a radioactive isotope). When in the form of a prodrug, a compound may be modified in vivo (e.g., intracellularly) after being administered to a patient or to a cell in culture. The modified compound (i.e., the processed prodrug) may be identical to a compound described herein and will be biologically active or have enough activity to be clinically beneficial. The same is true of a metabolite; a given compound may be modified within a cell and yet retain sufficient biological activity to be clinically useful.

Nucleic Acid-Based Therapeutics:

The therapeutic agents useful in treating the conditions described herein can also be nucleic acids. These nucleic acids can serve as the first agent that targets the HPA axis by inhibiting, directly or indirectly, the expression of CRH, ACTH, or cortisol, and they can serve as the second agent that targets the prefrontal cortex by increasing GABA. Where either or both of the first and second agents are used in combination with a third agent that inhibits the sympathetic nervous system, the "third" agent can be a nucleic acid that inhibits the expression of a neurotransmitter or its cognate receptor within the sympathetic nervous system (e.g., the nucleic acid can inhibit the expression of a β adrenergic receptor).

The nucleic acids can be "isolated" or "purified" (i.e., no longer associated with some or all of the flanking nucleic acid sequences or cellular components with which the nucleic acid is naturally associated in vivo). For example, with respect to a cell, tissue, or organism with which it was once naturally associated, a nucleic acid sequence useful as a therapeutic agent can be at least 50% pure (e.g., 60%, 70%, 75%, 80%, 85%, 90%, 95%, 98%, or 99% pure). Where a naturally occurring or modified nucleic acid sequence (e.g., a cDNA) is administered, it may include some of the 5' or 3' non-coding sequence associated with the naturally occurring gene. For example, an isolated nucleic acid (DNA or RNA) can include some or all of the 5' or 3' non-coding sequence that flanks the coding sequence (e.g., the DNA sequence that is transcribed into, or the RNA sequence that gives rise to, the promoter or an enhancer in the mRNA). For example, an isolated nucleic acid can contain less than about 5 kb (e.g., less than about 4 kb, 3 kb, 2 kb, 1 kb, 0.5 kb, or 0.1 kb) of the 5' and/or 3' sequence that naturally flanks the nucleic acid molecule in a cell in which the nucleic acid naturally occurs. In the event the nucleic acid is RNA or mRNA, it is "isolated" or "purified" from a natural source (e.g., a tissue) or a cell culture when it is substantially free of the cellular components with which it naturally associates in the cell and, if the cell was cultured, the cellular components and medium in which the cell was cultured (e.g., when the RNA or mRNA is in a form that contains less than about 20%, 10%, 5%, 1%, or less, of other cellular components or culture medium). When chemically synthesized, a nucleic acid (DNA or RNA) is "isolated" or "purified" when it is substantially free of the chemical precursors or other chemicals used in its synthesis (e.g., when the nucleic acid is in a form that contains less than about 20%, 10%, 5%, 1%, or less, of chemical precursors or other chemicals).

Nucleic acids useful in the compositions and methods described herein can be double-stranded or single-stranded and can, therefore, either be a sense strand, an antisense strand, or a portion (i.e., a fragment) of either the sense or the antisense strand. The nucleic acids can be synthesized using standard nucleotides or nucleotide analogs or derivatives (e.g., inosine, phosphorothioate, or acridine substituted nucleotides), which can alter the nucleic acid's ability to pair with complementary sequences or to resist nucleases. The stability or solubility of a nucleic acid can be altered (e.g., improved) by modifying the nucleic acid's base moiety, sugar moiety, or phosphate backbone. For example, the nucleic acids of the invention can be modified as taught by Toulmé (*Nature Biotech.* 19:17, 2001) or Faria et al. (*Nature Biotech.* 19:40-44, 2001), and the deoxyribose phosphate backbone of nucleic acids can be modified to generate peptide nucleic acids (PNAs; see Hyrup et al., *Bioorganic & Medicinal Chemistry* 4:5-23, 1996).

PNAs are nucleic acid "mimics;" the molecule's natural backbone is replaced by a pseudopeptide backbone and only the four nucleotide bases are retained. This allows specific hybridization to DNA and RNA under conditions of low ionic strength. PNAs can be synthesized using standard solid phase peptide synthesis protocols as described, for example by Hyrup et al. (supra) and Perry-O'Keefe et al. (*Proc. Natl. Acad. Sci. USA* 93:14670-675). PNAs of the nucleic acids described herein can be used in therapeutic and diagnostic applications. For example, PNAs can be used as antisense or antigene agents for sequence-specific modulation of gene expression by, for example, inducing transcription or translation arrest or inhibiting replication.

The nucleic acids can be incorporated into a vector (e.g., an autonomously replicating plasmid or virus) prior to administration to a patient, and such vectors are within the scope of the present invention. The invention also encompasses genetic constructs (e.g., plasmids, cosmids, and other vectors that transport nucleic acids) that include a nucleic acid of the invention in a sense or antisense orientation. The nucleic acids can be operably linked to a regulatory sequence (e.g., a promoter, enhancer, or other expression control sequence, such as a polyadenylation signal) that facilitates expression of the nucleic acid. The vector can replicate autonomously or integrate into a host genome, and can be a viral vector, such as a replication defective retrovirus, an adenovirus, or an adeno-associated virus. In addition, when present, the regulatory sequence can direct constitutive or tissue-specific expression of the nucleic acid.

The nucleic acids can be antisense oligonucleotides. While "antisense" to the coding strand of the targeted sequence, they need not bind to a coding sequence; they can also bind to a noncoding region (e.g., the 5' or 3' untranslated region). For example, the antisense oligonucleotide can be complementary to the region surrounding the translation start site of an mRNA (e.g., between the −10 and +10 regions of a target gene of interest or in or around the polyadenylation signal). Moreover, gene expression can be inhibited by targeting nucleotide sequences complementary to regulatory regions (e.g., promoters and/or enhancers) to form triple helical structures that prevent transcription of the gene in target cells (see generally, Helene, *Anticancer Drug Des.* 6:569-84, 1991; Helene, *Ann. N.Y. Acad. Sci.* 660:27-36, 1992; and Maher, *Bioassays* 14:807-15, 1992). The sequences that can be targeted successfully in this manner can be increased by creating a so-called "switchback" nucleic acid. Switchback molecules are synthesized in an alternating 5'-3', 3'-5' manner, such that they base pair with first one strand of a duplex and then the other, eliminating the necessity for a sizeable stretch of either purines or pyrimidines on one strand of a duplex.

Fragments having as few as 9-10 nucleotides (e.g., 12-14, 15-17, 18-20, 21-23, or 24-27 nucleotides; siRNAs typically have 21 nucleotides) can be useful and are within the scope of the invention.

In other embodiments, antisense nucleic acids can be anomeric nucleic acids, which form specific double-stranded hybrids with complementary RNA in which, contrary to the usual b-units, the strands run parallel to each other (Gaultier et al., *Nucleic Acids Res.* 15:6625-6641, 1987; see also Tanaka et al., *Nucl. Acids Res.* 22:3069-3074, 1994). Alternatively, antisense nucleic acids can comprise a 2'-o-methylribonucleotide (Inoue et al., *Nucleic Acids Res.* 15:6131-6148, 1987) or a chimeric RNA-DNA analogue (Inoue et al., *FEBS Lett.* 215:327-330, 1987).

Antibodies:

Antibodies and antigen binding fragments thereof useful as therapeutic agents in the present compositions. These antibodies may be of the G class (IgG), but IgM, IgD, IgA, and IgE antibodies can also be used; what is required is that the antibodies specifically bind a target described herein and alter that target—whether by enhancing or inhibiting its activity—in a way that, in accordance with our findings, confers a clinical benefit on a patient to whom they are administered. The antibodies can be polyclonal or monoclonal antibodies, and we use the terms "antibody" and "antibodies" to refer to whole antibodies or fragments thereof that are, or that include, an antigen-binding domain of the whole antibody. For example, useful antibodies can lack the Fc portion; can be single chain antibodies; or can be fragments consisting of (or consisting essentially of) the variable, antigen-binding domain of the antibody. The antibodies can be humanized (by, for example, CDR grafting) or fully human.

Methods of producing antibodies are well known in the art. For example, as noted above, human monoclonal antibodies can be generated in transgenic mice carrying the human immunoglobulin genes rather than those of the mouse. Splenocytes obtained from these mice (after immunization with an antigen of interest) can be used to produce hybridomas that secrete human mAbs with specific affinities for epitopes from a human protein (see, e.g., WO 91/00906, WO 91/10741; WO 92/03918; WO 92/03917; Lonberg et al., *Nature* 368:856-859, 1994; Green et al., *Nature Genet.* 7:13-21, 1994; Morrison et al. *Proc. Natl. Acad. Sci. USA* 81:6851-6855, 1994; Bruggeman et al., *Immunol.* 7:33-40, 1993; Tuaillon et al., *Proc. Natl. Acad. Sci. USA* 90:3720-3724, 1993; and Bruggeman et al., *Eur. J. Immunol* 21:1323-1326, 1991).

The antibody can also be one in which the variable region, or a portion thereof (e.g., a CDR), is generated in a non-human organism (e.g., a rat or mouse). Thus, the invention encompasses chimeric, CDR-grafted, and humanized antibodies and antibodies that are generated in a non-human organism and then modified (in, e.g., the variable framework or constant region) to decrease antigenicity in a human. Chimeric antibodies (i.e., antibodies in which different portions are derived from different animal species (e.g., the variable region of a murine mAb and the constant region of a human immunoglobulin) can be produced by recombinant techniques known in the art. For example, a gene encoding the Fc constant region of a murine (or other species) monoclonal antibody molecule can be digested with restriction enzymes to remove the region encoding the murine Fc, and the equivalent portion of a gene encoding a human Fc constant region can be substituted therefor (see European Patent Application Nos. 125,023; 184,187; 171,496; and 173,494; see also WO 86/01533; U.S. Pat. No. 4,816,567; Better et al., *Science* 240:1041-1043, 1988; Liu et al., *Proc. Natl. Acad. Sci. USA* 84:3439-3443, 1987; Liu et al., *J. Immunol.* 139:3521-3526, 1987; Sun et al., *Proc. Natl. Acad. Sci. USA* 84:214-218, 1987; Nishimura et al., *Cancer Res.* 47:999-1005, 1987; Wood et al., *Nature* 314:446-449, 1985; Shaw et al., *J. Natl. Cancer Inst.* 80:1553-1559, 1988; Morrison et al., *Proc. Natl. Acad. Sci. USA* 81:6851, 1984; Neuberger et al., *Nature* 312:604, 1984; and Takeda et al., *Nature* 314:452, 1984).

An antigen-binding fragment of the invention can be: (i) a Fab fragment (i.e., a monovalent fragment consisting of the VL, VH, CL and CH1 domains); (ii) a F(ab')$_2$ fragment (i.e., a bivalent fragment containing two Fab fragments linked by a disulfide bond at the hinge region); (iii) a Fd fragment consisting of the VH and CH1 domains; (iv) a Fv fragment consisting of the VL and VH domains of a single arm of an antibody, (v) a dAb fragment (Ward et al., *Nature* 341:544-546, 1989), which consists of a VH domain; and (vi) an isolated complementarity determining region (CDR).

Expression vectors can be used to produce the proteins of the invention, including antibodies, ex vivo (e.g., the proteins of the invention can be purified from expression systems such as those described herein) or in vivo (in, for example, whole organisms).

Formulations and Dosages:

The identified agents that target the HPA axis, the prefrontal cortex and/or the sympathetic nervous system can be administered to a patient at therapeutically effective doses to prevent, treat or ameliorate any of the disorders or conditions described herein (e.g., an addiction, obesity, post-traumatic stress disorder or an associated condition). A therapeutically effective dose refers to an amount of the agent or combination of agents sufficient to improve at least one of the signs or symptoms of the disorder or condition.

Many of the agents useful in the context of the present invention have been used previously to treat patients for other reasons. Where dosing information is available, it can be used to help determine effective doses of the agents in the presently described combinations. The dose used to treat a patient for an addiction, one of the other disorders described herein, and/or a related condition, can be the same as the dose that has been used previously for another indication. The doses may also differ. For example, the effective dosages required in connection with the combination therapies described herein may be less than those previously proven safe and effective.

Toxicity and therapeutic efficacy of the agents described herein can be determined, as necessary, by standard pharmaceutical procedures in cell cultures or experimental animals. For example, laboratory animals such as rodents and non-human primates can be used to determine the $LD_{50}$ (the dose lethal to 50% of the population) and the $ED_{50}$ (the dose therapeutically effective in 50% of the population). The dose ratio between toxic and therapeutic effects is the therapeutic index, which can be expressed as the ratio $LD_{50}$:$ED_{50}$. Compounds that exhibit large therapeutic indices are typically preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays (e.g., assays designed to determine whether a nucleic acid, nucleic acid-based agent, or a protein such as an antibody inhibits (or stimulates) the expression or activity of the ligand or receptor it is intended to inhibit (or stimulate)).

A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses (e.g., therapeutically effective doses) in humans. Levels in plasma can be measured, for example, by high performance liquid chromatography.

One of the greatest concerns in the treatment of drug addiction is the high rate of recidivism. This phenomenon can be tested in animals during reinstatement, which is a widely regarded preclinical model of the propensity to relapse to drug taking, and animal models of reinstatement can be used to further determine and define effective doses of the agents described herein. For example, animals can be taught to self-administer a drug until stable drug intake is maintained and then subjected to prolonged periods of extinction training or abstinence. Once the criteria for extinction are met, or following a specified period of abstinence, the ability of specific stimuli to reinstate responding on the manipulandum previously associated with the delivery of drug infusions is taken as a measure of drug seeking. This reinstatement of drug-seeking behavior can be elicited by priming injections of the drug itself in rats and monkeys (Stewart, *J. Psychiatr: Neurosci.* 25:125-136, 2000) or by exposure to brief periods of intermittent electric footshock in rats (Shaham et al., *Brain Res. Rev.* 33:13-33, 2000; Stewart, *J. Psychiatr. Neurosci.* 25:125-136, 2000). Acute re-exposure to the self-administered drug (de Wit, *Exp. Clin. Psychopharmacol.* 4:5-10, 1996) and exposure to stress (Shiffman and Wills, *Coping and Substance Abuse*, Academic Press, Orlando, 1985; Lamon and Alonzo, *Addict. Behav.* 22:195-205, 1997; Brady and Sonne, *Alc. Res. Health* 23:263-271, 1999; Sinha, *Psychopharmacol.* 158:343-359, 2001; and Sinha et al., *Psychopharmacol.* 142:343-351, 1999), or simply the presentation of stress-related imagery (Sinha et al., *Psychopharmacol.* 158:343-359, 2000), have also been identified as potent events for provoking relapse to drug seeking in humans.

In the studies described below, we initially found a dose of each of metyrapone and oxazepam that reduced cocaine self-administration without producing nonspecific debilitating effects on other behaviors. We then reduced the dose by one-half until we found a dose of each drug that no longer affected cocaine self-administration or any other observable behaviors (i.e., an ineffective dose). When we then combined the ineffective doses of the two drugs, cocaine self-administration was reduced. This suggests that although the two drugs produce their effects through different mechanisms, the effects are additive. Thus, we concluded that combining drugs that affect the HPA axis through different mechanisms can produce an additive effect on cocaine reward. Furthermore, by combining these drugs at concentrations that have no effect when the drugs are administered alone, we can minimize the potential toxic side effects (e.g., excessive decreases in plasma cortisol with metyrapone and the abuse liability of benzodiazepines) that may be associated with these compounds. Accordingly, the compositions of the present invention may include combinations of therapeutic agents, one or both of which are present at a dosage level lower than that which would be required to achieve an effect had the agent been administered alone; the dosages may be additive.

Pharmaceutical compositions for use in accordance with the present invention can be formulated in any conventional manner using one or more physiologically acceptable carriers or excipients. Thus, the agents, including compounds and their physiologically acceptable salts and solvates, can be formulated for administration by or oral or parenteral administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound(s) (which we may refer to herein as "therapeutic agent(s)").

The agents, including compounds (e.g., small organic molecules) can be formulated for parenteral administration by injection (e.g., by bolus injection or continuous infusion). Formulations for injection can be presented in unit dosage form, (e.g., in ampoules or in multi-dose containers) with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle (e.g., sterile pyrogen-free water) before use.

In addition to the formulations described previously, the agents can also be formulated as a depot preparation. Such long acting formulations can be administered by implantation (for example, subcutaneously or intramuscularly) or by intramuscular injection. Thus, for example, the agents can be formulated with suitable polymeric or hydrophobic materials (for example as an emulsion in an acceptable oil) or ion exchange resins, or as sparingly soluble derivatives, for example, as a sparingly soluble salt.

The compositions can also be formulated for other routes of administration, including intranasal, topical, and mucosal (e.g., by sublingual administration).

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration. Various presentation forms (e.g., presentation by way of packs and dispensers) are within the scope of the present invention.

Nucleic acids, including antisense nucleic acids, can also be administered systemically and, if so, may be modified to target selected cells within the HPA axis, the prefrontal cortex and/or the sympathetic nervous system. For example, antisense nucleic acids can be linked to antibodies or other proteins (e.g., receptor ligands) that will specifically bind to cell surface receptors or other components associated with the target cell type. Similarly, the nucleic acids can include agents that facilitate their transport across the cell membrane (see, e.g., Letsinger et al., *Proc. Natl. Acad. Sci. USA* 86:6553-6556, 1989; Lemaitre et al., *Proc. Natl. Acad. Sci. USA* 84:648-652, 1987; and WO 88/09810) or the blood-brain barrier (see, e.g., WO 89/10134). In addition, nucleic acids can be modified with intercalating agents (Zon, *Pharm. Res.* 5:539-549, 1988). Antisense nucleic acids can also be delivered to cells using the vectors described herein. To achieve sufficient intracellular concentrations of antisense nucleic acids, one can express them in vectors having a strong promoter (e.g., a strong pol II or pol III promoter).

In specific embodiments, the invention features pharmaceutical compositions that include a first agent that targets the HPA axis and a second agent that targets the prefrontal cortex. The first agent can be an agent that inhibits CRH, that inhibits ACTH, and/or that inhibits cortisol and the second agent can be an agent that increases the expression, secretion, or activity of GABA, is a GABA mimic, and/or inhibits GABA metabolism. Either the first and/or the second agent can be a chemical compound. For example, the first agent can be metyrapone (Metopirone®) or ketoconazole (Nizoral®) or a salt, solvate, hydrate, prodrug, structural analog, or polymorph thereof. The second agent can be a benzodiazepine (e.g., oxazepam or chlordiazepoxide) or a salt, solvate, hydrate, prodrug, structural analog, or polymorph thereof. The second agent can also be mirtazapine or atomoxetine or salts, solvates, hydrates, prodrugs, structural analogs, or polymorphs thereof. Another useful second agent is gabapentin (Neurontin™) or a salt, solvate, hydrate, prodrug, structural analog, or polymorph thereof, or is muscimol or baclofen or salts, solvates, hydrates, prodrugs, structural analogs, or polymorphs thereof. Additional useful second agents are: progabide, riluzole, baclofen, vigabatrin, valproic acid (Depakote™), tiagabine (Gabitril™), lamotrigine (Lamictal™), phenytoin (Dilantin™), carbamazepine (Tegretol™), and topiramate (Topamax™) or salts, solvates, hydrates, prodrugs, structural analogs, or polymorphs thereof. Any of the pharmaceutical compositions can be formulated for oral administration or for intravenous administration. The amount of the first agent or the amount of the second agent in a unit dosage can be less than the amount of the first agent or the second agent currently or typically prescribed for a patient requiring the same unit dosage. Combining the agents may allow them to be administered at dosages that are lower than expected given current, commonly prescribed dosages. For example, a pharmaceutical composition can include about 5-60 mg of oxazepam and about 250-1000 mg of metyrapone (Metopirone®) in unit dosage form. Any of these compositions can further include a third agent that inhibits activity in the sympathetic nervous system. The third agent can be a beta blocker (e.g., sotalol (Betapace®), imolol (Blocadren®), carteolol (Cartrol®), carvedilol (Coreg®), nadolol (Corgard®), nadol/bendroflunetazide (Corzide®), propranolol (Inderal®), propranolol/HCTZ (Inderide®), betaxolol (Kerlone®), penbutolol (Levatol®), metoprolol (Lopressor®), labetalol (Normodyne®), acebutolol (Sectral®), atenolol/HCTZ (Tenoretic®), atenolol (Tenormin®), timolol/HCTZ (Timolide®), metoprolol (Toprol®), labetalol (Trandate®), pindolol (Visken®), bisoprolol (Zebeta®), bisoprolol/HCTZ (Ziac®), or esmolol (Brevibloc®)) or other anxiolytic compound (e.g., an SSRI such as citalopram (Celexa®), escitalopram oxalate (Lexapro®), fluvoxamine (Luvox®), paroxetine (Paxil®), fluoxetine (Prozac®), or sertraline (Zoloft®)). The anxiolytic compound or agent can also be an angiotensin II inhibitor (e.g., candasartan (Atacand®), eprosartan (Teveten®), irbesartan (Avapro®), losartan (Cozaar®), telmisartan (Micardis®), or valsartan (Diovan®)).

Concentrated compositions, suitable for shipment, storage, and later dilution are also within the invention.

The pharmaceutical compositions described above can be used in the methods described herein, including those that follow, and for the purposes of use described below (e.g. for use in the preparation of a medicament and/or in the preparation of a medicament for treating a disorder or condition described herein).

Methods of Treatment:

As noted, the compositions described herein can be used to treat patients suffering from a disorder associated with aberrant activity in the HPA axis. The treatment methods can include various steps, one of which can constitute identifying a patient in need of treatment. Physicians are well able to examine and diagnose patients suspected of suffering from addiction and/or another of the conditions described herein. Following a diagnosis, which may be made in the alternative, the physician can prescribe a therapeutically effective amount of a composition (e.g., a pharmaceutical composition comprising a first agent that targets the HPA axis and a second agent that targets the prefrontal cortex). The patient may have, or be diagnosed as having, an addiction to a substance such as alcohol, a chemical stimulant, a prescription (or prescribed) pain reliever, or a naturally-occurring plant-derived drug. The chemical stimulant can be cocaine, an amphetamine, methamphetamine, or crystalline methylamphetamine hydrochloride, or methylphenidate. Where analogs of specific drugs are addictive, addictions to those analogs can also be treated.

The drug can also be a barbiturate (e.g., thiamyl (Surital®), thiopental (Pentothal®), amobarbital (Amyta®), pentobarbital (Nembutal®), secobarbital (Seconal®), Tuinal (an amobarbital/secobarbital combination product), butalbital (Fiorina®), butabarbital (Butisol®), talbutal (Lotusate®), aprobarbital (Alurate®), phenobarbital (Luminal®), and mephobarbital (Mebaral®)), or opiate (e.g., heroin, codeine, hydrocodone).

Naturally-occurring plant-derived drugs include marijuana and tobacco. The compositions described herein can be used to treat patients addicted to these substances generally and/or to a more specific ingredient therein (e.g., the nicotine in tobacco). The addiction may also manifest as addiction to an activity such as gambling, sex or a sexual activity, or overeating (which may be associated with an eating disorder or may result in obesity). More generally, eating and sleeping disorders are among those amenable to treatment with the present compositions. Eating disorders include anorexia nervosa, bulimia nervosa, binge eating disorder and eating disorders not otherwise specified (EDNOS). Several studies have examined the function of the HPA axis in anorexia nervosa. A principal finding is that of hypercortisolism, associated with increased central corticotrophin-releasing hormone levels and normal circulating levels of adrenocorticotropic hormone. While anorexia nervosa can be difficult to diagnose, patients with this disorder present with endocrine dysfunction, often evident as amenorrhea, abnormal temperature regulation, abnormal growth hormone levels, and abnormal eating. The present methods can include a step of identifying a patient in need of treatment, and these characteristics would be, or would likely be among, those used by physicians to diagnose anorexia nervosa.

The present compositions can be used to treat patients who have Prader Willi syndrome, and methods of treating such patients are within the scope of the invention.

Sleep disorders include insomnia, sleep apnea sleep disorder, Restless Legs Syndrome (RLS) and Periodic Limb Movement Disorder (PLMD), and narcolepsy.

Other patients amenable to treatment include those suffering from anxiety (which may be associated with panic disorder, obsessive compulsive disorder (OCD), post-traumatic stress disorder (PTSD), social anxiety disorder, or may be a generalized anxiety disorder). Where the condition is depression, it may be depression associated with major depressive disorder or dysthymia, bipolar depression, or may be associated with a medical condition or substance abuse. The risk of developing depression or other major affective disorders is determined by a complex interplay between genetic susceptibility, environmental exposures, and aging.

Other patients amenable to treatment include those suffering from schizophrenia; those with an attention-deficit disorder (e.g., ADD or ADHD); those experiencing menopause; and those suffering from a menstrual cycle-related syndrome (e.g., PMS).

The disorders and events described herein may be variously categorized and may be related to one another in various ways. For example, social anxiety may contribute to an eating disorder and other anxiety-associated conditions, such as PTDSs, may manifest as a sleep disorder. Patients diagnosed as clinically depressed may also experience sleep disorders. Addiction, which has been characterized as a progressive disorder, may begin with the self-administration of a prescription or non-prescription drug to alleviate a symptom of another neuropsychiatric disorder. For example, a patient may self-administer alcohol or marijuana in the event of a depression or anxiety or a sleep-aid to treat the difficulty in sleeping as a result thereof. The relationships between the disorders and related conditions or symptoms may flow in different directions as well. For example, chronic activation of the HPA axis in insomnia puts insomniacs at risk not only for mental disorders (i.e., chronic anxiety and depression), but also for significant medical morbidity associated with such activation. Insomnia is, by far, the most commonly encountered sleep disorder in medical practice. Either as a symptom of various psychiatric or medical disorders or as the result of a stressful situation, chronic and severe insomnia is perceived by the patient as a distinct disorder (see Vgontzas et al., *J. Clin. Endocrinol. Metabl.* 86:3787-3794, 2006). Sleep disorders, including insomnia, can occur during menopause or when a patient is suffering from PMS.

Just as there can be some overlap in the categorization of the indications described herein, there can be some overlap in the nature of the agents applied and/or the manner in which they are categorized. For example, and as noted above, benzodiazepines can be used as the "second" agent to target the prefrontal cortex. Benzodiazepines can also be categorized as anti-anxiety drugs and therefore are suitable as the "third" agent described herein.

The success of the treatment can be assessed in a variety of ways, including objective measures (e.g., where the patient is addicted to a substance or activity, a reduction in the frequency or severity of drug self-administration or other addictive activity), a general improvement in health (e.g., an improvement in blood pressure, kidney function, liver function, or blood count) and/or subjective measures (e.g., a patient's report of reduced craving for a substance or activity or a better sense of well-being (e.g., where the patient suffers from anxiety or an anxiety-related disorder, a report of reduced anxiety, an improved mood, a greater sense of well-being, or an improved ability to cope with daily stressors)). Where the condition treated is an eating disorder or sleep disorder, treatment can be assessed by judging the effective return of (or return toward) normal eating or sleeping patterns.

In specific embodiments, the invention features methods of treating a patient who is suffering from a disorder associated with aberrant activity in the HPA axis. The method can include the steps of: (a) identifying a patient in need of treatment; and (b) administering to the patient a therapeutically effective amount of a composition described herein. The disorder can include addiction, anxiety, schizophrenia, or depression; the disorder can be an addiction to a substance (e.g., a chemical stimulant such as an opiate (e.g., heroin, codeine, hydrocodone, or analogs thereof), nicotine, alcohol, prescription pain reliever, or naturally-occurring plant-derived drug, such as nicotine). The chemical stimulant can also be cocaine, an amphetamine, a methamphetamine, methylphenidate, or analogs thereof.

The disorder can also be an addiction to an activity such as gambling or engaging in a sexual activity or excessive eating.

Where the patient is suffering from anxiety, the anxiety may be associated with a panic disorder, an obsessive compulsive disorder (OCD), a post-traumatic stress disorder (PTSD), a social anxiety disorder, or a generalized anxiety disorder. Where the patient is suffering from depression, the depression can be associated with major depressive disorder or dysthymia, with a bipolar depression, or a medical condition or substance abuse. As noted, the disorder can also be an eating disorder or a sleep disorder or a disruptive behavior disorder.

The methods can be carried out in treating a patient who is suffering from an unwanted symptom of menopause or the menstrual cycle by: (a) identifying a patient in need of treatment; and (b) administering to the patient a therapeutically effective amount of a composition described herein. The amounts of the compositions delivered are therapeutically effective, with effectiveness judged by relief in symptoms, which may include anxiety, depression, or difficulty sleeping.

The invention features the use of the compositions described herein in the preparation of a medicament. The invention further features the use of the compositions described herein in the preparation of a medicament for the treatment of obesity; an eating disorder; a sleep disorder; depression; a disruptive behavior disorder; schizophrenia; and/or anxiety, regardless of context.

EXAMPLES

Effects of Low Dose Combination Pharmacotherapy on Cocaine Self-Administration in Rats The studies described here examine a combination pharmacotherapy, consistent with that described herein, for the treatment of addiction (more specifically, cocaine abuse). Using this approach, two compounds, which are believed to use divergent mechanisms of action to ultimately produce similar effects on the body's responses to stressors, are administered together at doses that are ineffective, or much less effective, alone. Adult male Wistar rats were trained under a multiple, alternating schedule of cocaine and food self-administration. This schedule consisted of alternating periods of cocaine access and food reinforcement. In some instances, as described further below, three doses of cocaine (0.125, 0.25, or 0.50 mg/kg/infusion) were tested. Rats were also periodically trained with saline substitution (cocaine extinction) and food extinction during the same session.

These studies support the conclusion that pretreatment with the corticosterone synthesis inhibitors metyrapone and ketoconazole, the benzodiazepines chlordiazepoxide, alprazolam and oxazepam, and the CRH receptor antagonist CP-154,526 all decrease cocaine self-administration and the reinstatement of extinguished cocaine seeking in rats. We believe the combination pharmacotherapy reduces the likelihood of relapse by attenuating cue-induced increases in activity within the HPA axis, thereby reducing the cue-induced secretion of CRH, ACTH and cortisol (corticosterone), and by decreasing cue-induced alterations in activity in the prefrontal cortex.

Combinations Tested:

The combinations of drugs we tested include: (1) metyrapone and oxazepam; (2) ketoconazole and alprazolam; (3) ketoconazole and oxazepam; (4) metyrapone and alprazolam; (5) muscimol and CP-154,526; and (6) muscimol and metyrapone. The drug combinations consist of at least one drug from each class (e.g., metyrapone and oxazepam). As noted, the drugs were combined at doses below their normally effective doses, and an additive or synergistic effect emerged.

Training to Self-Administer Cocaine:

In our model, rats were exposed to alternating 15-minute periods of access to cocaine self-administration and food reinforcement. Food was used to control for potential nonspecific, ataxis effects of the drugs and combinations. The ideal drug or drug combination is one that reduces cocaine self-administration without affecting food-maintained responding. The other preclinical model we used is the cue-induced reinstatement of extinguished cocaine seeking model of relapse. In this model, rats are trained to self-administer cocaine and the ability of conditioned cues in the environment to reinstate extinguished responding is assessed and taken as a measure of relapse.

More specifically, adult male Wistar rats were implanted with chronic jugular catheters. Following recovery from surgery, the rats were trained to respond under a multiple, alternating schedule of food reinforcement and cocaine self-administration. Food-maintained responding was used to control for the non-specific motor effects of the various treatments. During the food component of the schedule, the stimulus light located above the food response lever was illuminated to indicate the availability of food reinforcement. Initially, each depression of the food response lever resulted in a brief darkening of the food stimulus light (0.6 seconds) and the delivery of a food pellet (45 mg). A 25-second timeout followed the delivery of each food pellet. During this timeout, the stimulus light was darkened and responses on the food lever were counted but had no scheduled consequences. Responding on the other (cocaine) lever during the food component also had no scheduled consequences. The response requirement for the food lever was gradually increased over several sessions from continuous reinforcement to a fixed-ratio four schedule whereby four responses were required for food presentation. Following 15 minutes of access to food, all stimulus lights in the chamber were darkened for a 1-minute timeout. Following the timeout, the stimulus light above the cocaine response lever was illuminated to indicate the availability of cocaine (0.125, 0.25, or 0.5 mg/kg/infusion). Initially, each depression of the cocaine response lever resulted in a brief darkening of the stimulus light and an infusion of cocaine (200 µl delivered over 5.6 seconds). A 20-second timeout period followed each infusion. The response requirement for cocaine was gradually increased to a fixed-ratio four schedule of reinforcement. After 15 minutes of access to cocaine and a 1-minute timeout, the rats were again allowed 15 minutes access to the food component of the schedule. Access to food and cocaine alternated in this manner every 15 minutes during the two hour behavioral sessions so that each rat was exposed to food and cocaine for four 15-minute periods each. Each behavioral session began with 15 minutes access to either food or cocaine, and this alternated daily. Stable baselines of responding were established when the total number of cocaine and food presentations, as well as the number of presentations during each of the four exposures each session, varied less than 10% for three consecutive sessions. At least three different doses of cocaine (e.g., 0.125, 0.25, and 0.5 mg/kg/infusion) were tested. Rats were first trained to self-administer 0.25 mg/kg/infusion, our standard dose of cocaine. When responding stabilized, the dose was changed to 0.125 or 0.5 mg/kg/infusion as appropriate. We have found that initially training rats with this moderated dose of cocaine (i.e., 0.25 mg/kg/infusion) hastens stability with the lower dose (i.e., 0.125 mg/kg/infusion).

Once stable baselines of responding were obtained, dose-response curves for the various compounds were individually generated for each rat. Rats were treated with each dose at least twice with a minimum of two days of baseline cocaine self-administration interspersed between each test. Each group of rats was tested with only two of the test compounds to minimize potential carryover effects. The minimally effective dose that reduced cocaine self-administration by at least 50% without affecting food-maintained responding (i.e., the high dose) was determined for each compound. The dose selected for the drug combination experiments was one-half of the minimally effective dose, and this dose had to also produce less than a 10% decrease in cocaine self-administration (i.e., an ineffective dose). If one-half of the minimally effective dose reduced cocaine self-administration by more than 10%, then the dose was once again reduced by one-half. For example, the minimally effective dose of ketoconazole was 25 mg/kg, and we have successfully used 12.5 mg/kg in our studies with alprazolam and oxazepam. This dose (12.5 mg/kg) has no effect on cocaine- or food-maintained responding when tested alone, but significantly reduces cocaine self-administration when combined with a similarly ineffective dose of alprazolam (i.e., 1.0 mg/kg, ip) or oxazepam (10 mg/kg, ip). This rationale guided the selection of the doses of each of the compounds in the combination studies. Each experimental group consisted of between 8 and 10 rats.

Cue-Induced Reinstatement of Extinguished Cocaine Seeking:

The experiments described herein were designed to investigate whether or not drug combinations identified as effective in reducing cocaine self-administration would also block the ability of conditioned cues to reinstate extinguished cocaine-seeking behavior. Adult male Wistar rats were implanted with chronic jugular catheters and trained to self-administer cocaine (0.25 mg/kg/infusion) by pressing one of the response levers in the experimental chamber (i.e., the "active" or "cocaine" lever) under a fixed-ratio four (FR4)

schedule of reinforcement during daily 2-hour sessions conducted 5 days per week. At the start of each session, both levers were extended into the chamber and the stimulus light above the active lever was illuminated to indicate the availability of cocaine. Initially, each depression of the active lever resulted in an intravenous infusion of cocaine and the concurrent presentation of a house light and tone compound stimulus (i.e., the conditioned cue or secondary reinforcer). A 20-second timeout period followed each infusion. The stimulus light above the active lever and the house light and tone compound stimulus were extinguished during the timeout period, and the light above the active lever was illuminated once the timeout ended. When responding on the active lever varied less than 20% for two consecutive days, the response requirement was increased to FR2. When similar stability was observed under the FR2 schedule or reinforcement, the response requirement was increased to the final ratio of four. The criteria for stable responding under the FR4 schedule of reinforcement was a minimum of 10 days of exposure to this schedule that concluded with at least three consecutive days when responding varied by less than 10%. Responses on the inactive lever were counted but resulted in no programmed consequences at any time. Once stable cocaine self-administration was observed, rats were exposed to extinction; the rats were placed into the behavioral chambers, but responding on the "cocaine" (active) lever produced no programmed consequences. Extinction training continued until responding decreased to less than 20% of baseline self-administration. Then reinstatement testing commenced. The rats were placed into the experimental chambers, both response levers were extended into the chamber, and the stimulus light above the "active" lever was illuminated as during self-administration training. During reinstatement, responding on the "active" lever resulted in a 5.6-second presentation of the conditioned reinforcer (i.e., the house light and tone compound stimulus that had been paired with cocaine during self-administration). Responses on the "inactive" lever were counted but resulted in no scheduled consequences. Responding on the "active" lever during reinstatement testing was taken as an index of cocaine-seeking behavior. Each experimental group consisted of 8 to 10 rats.

The Effect of Metyrapone and Oxazepam on Intravenous Self-Administration of Cocaine:

These experiments were designed to determine the effects of a combination of metyrapone and oxazepam on intravenous cocaine self-administration in rats responding under a multiple, alternating schedule of food reinforcement and cocaine self-administration. The results are depicted in the graph of FIG. 1A. The first bar to the left ("Ext") shows the results of extinction when responding on the "active" lever only resulted in infusions of saline. The second bar ("Veh") depicts the number of cocaine infusions self-administered following pretreatment with the vehicle (5% emulphor in 0.9% saline) for the treatment drugs. The "Met-high" bar shows the number of infusions of cocaine following pretreatment with the high dose of metyrapone (25-175 mg/kg, ip), while the "OX-high" bar depicts the number of cocaine infusions self-administered following pretreatment with the high dose of oxazepam (5-80 mg/kg, ip).

Both metyrapone and oxazepam reduced cocaine self-administration without affecting food-maintained responding at these doses. The "Met-low" and "OX-low" bars represent responding following pretreatment with the low, ineffective doses (oxazepam 5-25 mg/kg, ip; metyrapone 25-50 mg/kg, ip) of metyrapone and oxazepam alone. Clearly, these doses did not significantly affect cocaine self-administration (or food-maintained responding) when administered alone. The "COM-low" bar depicts the number of cocaine infusions self-administered following the delivery of the combination pharmacotherapy (i.e., an injection consisting of the ineffective doses of metyrapone and oxazepam). As can be seen, the combination pharmacotherapy consisting of metyrapone and oxazepam reduced cocaine self-administration to levels seen when only saline was delivered when the active lever was pressed during extinction. The combination pharmacotherapy reduced cocaine self-administration to extinction levels without affecting food-maintained responding, suggesting that the combination was reducing the motivation to seek cocaine without affecting responding or the motivation for another reinforcer (i.e., food).

Figure 1B:
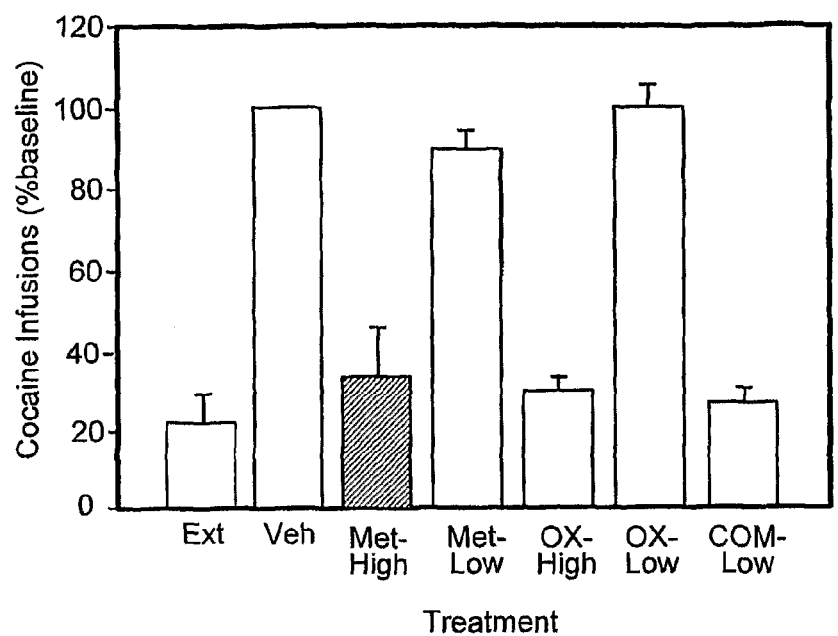

FIG. 1B depicts the same data as shown in FIG. 1A, but the data are presented as the percentage of baseline infusions under the conditions tested. The "high" dose of metyrapone and oxazepam reduced cocaine self-administration to less than 50% of baseline self-administration, while the "low" doses only reduced self-administration by 10% or less. As in FIG. 1A, the combination of the low doses of oxazepam and metyrapone reduced cocaine self-administration to levels seen during extinction.

Figure 2A:
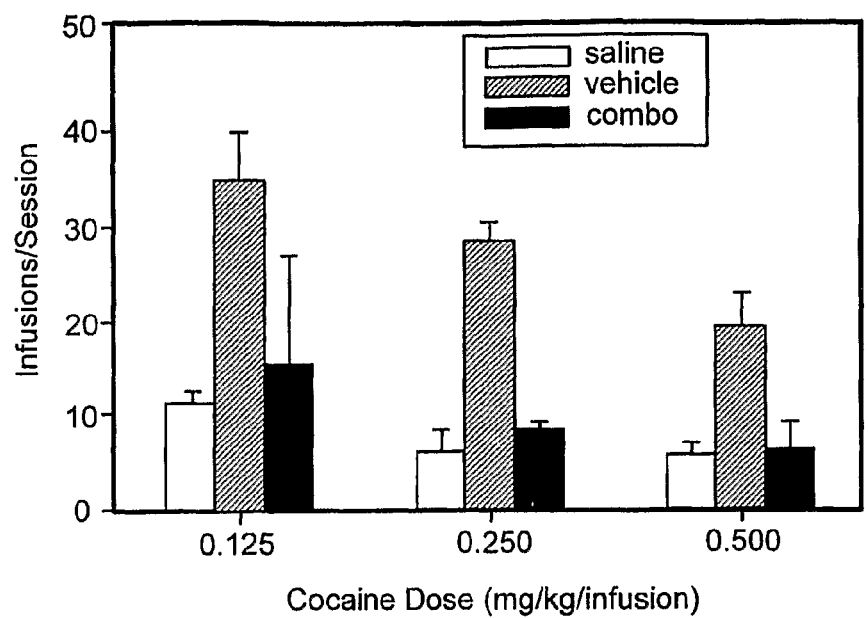
FIGS. 2A and 2B are bar graphs illustrating the effect of the combination of metyrapone and oxazepam on intravenous self-administration of three different doses of cocaine in rats. The number of infusions per session is plotted in FIG. 1A, and the same result, expressed as a percentage of the base, is plotted in FIG. 2B.

FIG. 2A depicts experiments designed to investigate the effects of the combination of the ineffective doses of metyrapone and oxazepam on cocaine self-administration when different groups of rats were trained to self-administer different doses of cocaine. It is important to determine whether or not the rats could overcome the effects of the combination when higher doses of cocaine were available. This would be analogous to a cocaine addict increasing his or her intake of cocaine to overcome the effects of the combination pharmacotherapy. The numbers on the X-axis represent the three doses of cocaine that were self-administered. "Saline" shows the number of infusions self-administered when only saline was in the syringe (i.e., extinction). "Vehicle" represents the number of cocaine infusions self-administered when the vehicle (5% emulphor in 0.9% saline) for the treatment of drugs was delivered prior to the start of the cocaine self-administration session. "Combo" depicts the number of cocaine infusions self-administered following pretreatment with the combination of the ineffective doses of metyrapone and oxazepam. Clearly, this combination reduced cocaine self-administration to extinction levels regardless of the dose of cocaine that was available for self-administration. This indicates that the effects of the combination pharmacotherapy would not easily be overcome by increasing the intake or dose of cocaine.

Figure 2B:
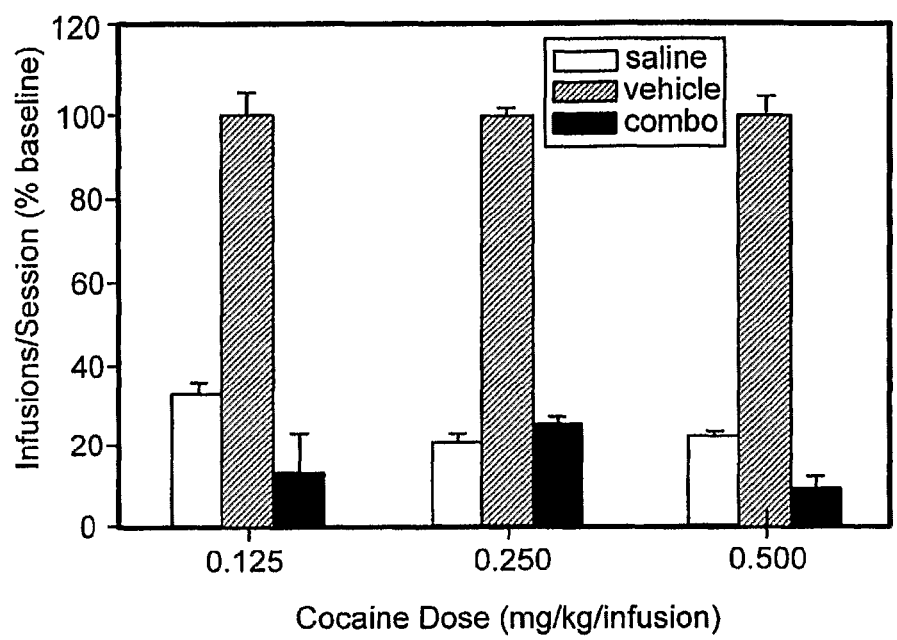

FIG. 2B depicts the same data as in FIG. 2A, but the data are presented as the percentage of baseline infusions under the different conditions. FIG. 2A shows that the combination of the low doses of oxazepam and metyrapone reduced cocaine self-administration to levels seen during extinction regardless of the dose of cocaine that was available for self-administration.

Figure 10:
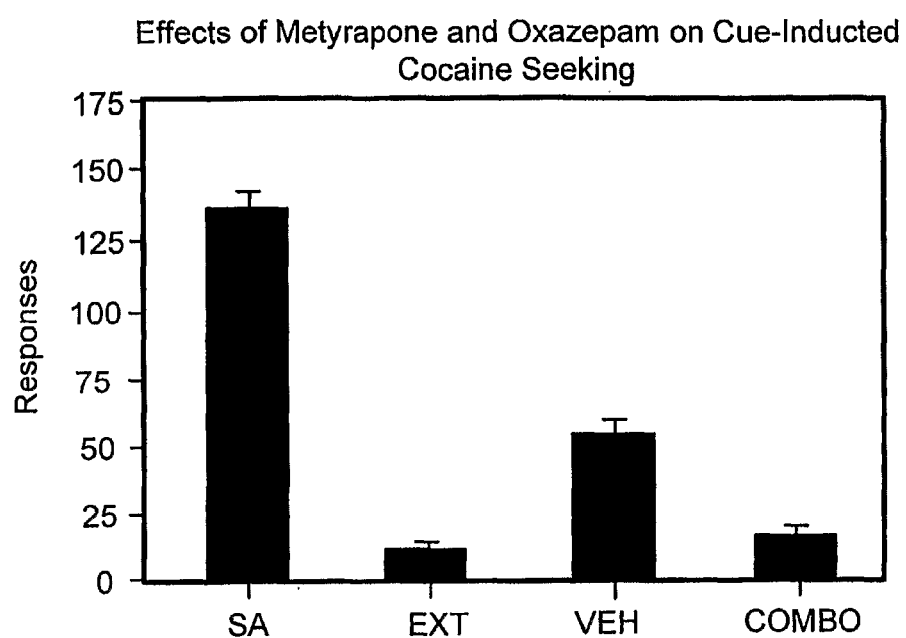
FIG. 10 is a bar graph illustrating the effect of the combination of metyrapone and oxazepam on the cue-induced reinstatement of extinguished cocaine-seeking behavior in rats.

We also conducted experiments to determine the effect of a combination of metyrapone and oxazepam on the cue-induced reinstatement of extinguished cocaine seeking in rats. We used an animal model of the relapse to cocaine seeking. Referring to FIG. 10, the bar labeled "SA" depicts the number of responses made on the "active" lever during cocaine self-administration. The bar labeled "EXT" depicts the number of responses on the "active" lever during extinction when responding on this lever only resulted in infusions of saline. The third bar, "VEH", represents responding on the "active" lever during reinstatement testing following pretreatment with the vehicle (5% emulphor in 0.9% saline) for the treatment drugs. The last bar, "COMBO", depicts the number of responses on the "active" lever during reinstatement testing following the delivery of the combination pharmacotherapy (i.e., an injection consisting of the ineffective doses of metyrapone and oxazepam as determined in the cocaine self-administration experiments (see FIG. 1A). The combination pharmacotherapy reduced cocaine seeking (i.e., responding on the active lever during reinstatement) to levels seen when only saline was delivered when the active lever was pressed during extinction. The combination therapy reduced reinstatement (relapse) to extinction levels without affecting food-maintained responding. This suggests that the combination reduced the motivation to seek cocaine without affecting responding or motivation for another reinforcer (i.e., food).

Figure 3:
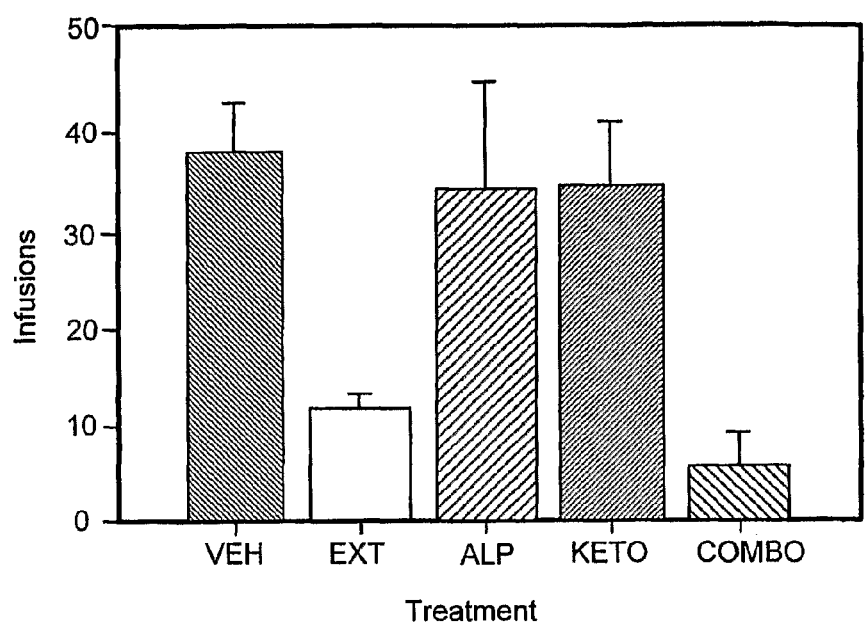
FIG. 3 is a bar graph illustrating the effect of the combination of ketoconazole and alprazolam on intravenous cocaine self-administration in rats. The number of infusions is plotted.

The Effect of Ketoconazole and Alprazolam on Intravenous Self-Administration of Cocaine:

These experiments were designed to determine the effects of a combination of ketoconazole and alprazolam on intravenous cocaine self-administration in rats responding under a multiple, alternating schedule of food reinforcement and cocaine self-administration. The data are presented in FIG. 3. The solid bar ("VEH") depicts the number of cocaine infusions self-administered following pretreatment with the vehicle (5% emulphor in 0.9% saline). The open bar ("EXT") shows the results of extinction when responding on the "active" lever only resulted in infusions of saline. The "ALP" (striped) and "KETO" (lightly shaded) bars represent self-administration following pretreatment with the low, ineffective doses (alprazolam 0.2-2 mg/kg, ip; ketoconazole 5-75 mg/kg, ip) of alprazolam and ketoconazole alone. Clearly, these doses did not significantly affect cocaine self-administration (or food-maintained responding) when administered alone. The "COMBO" (small striped) bar depicts the number of cocaine infusions self-administered following the delivery of the combination pharmacotherapy (i.e., an injection consisting of the ineffective doses of alprazolam and ketoconazole). As can be clearly seen, the combination pharmacotherapy consisting of alprazolam and ketoconazole reduced cocaine self-administration to levels seen when only saline was delivered when the active lever was pressed during extinction. The combination pharmacotherapy reduced cocaine self-administration to extinction levels without affecting food-maintained responding. This suggests that the combination was reducing the motivation to seek cocaine without affecting responding or motivation for another reinforcer (i.e., food). These data also demonstrate that the effects of the combination pharmacotherapy are observed with at least two different corticosterone synthesis inhibitors and two different benzodiazepines.

Figure 4:
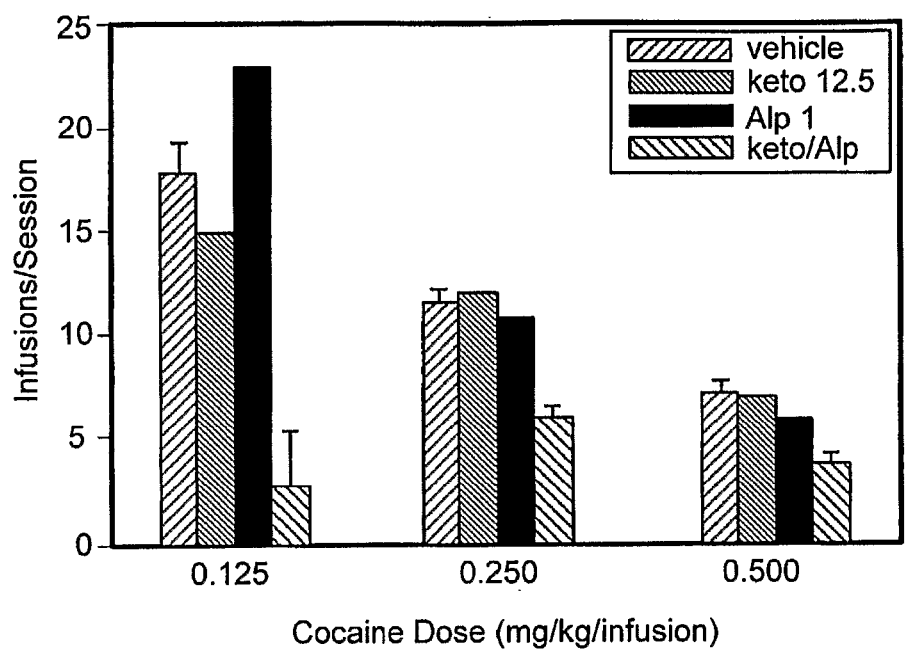
FIG. 4 is a bar graph illustrating the effect of the combination of ketoconazole and alprazolam on intravenous self-administration of three different doses of cocaine in rats.

Referring to FIG. 4, we see the results of experiments designed to investigate the effects of the combination of ineffective doses of ketoconazole (e.g., 12.5 mg/kg, ip) and alprazolam (e.g., 1 mg/kg, ip) on cocaine self-administration when different groups of rats were trained to self-administer different doses of cocaine. This is important for the same reason as provided above in our studies with metyrapone and oxazepam. The numbers on the X-axis represent the three doses of cocaine that were self-administered. "Vehicle" shows the number of infusions self-administered when the vehicle (5% emulphor in 0.9% saline) was delivered. "Keto 12.5" depicts the number of cocaine infusions self-administered following the delivery of the ineffective doses of ketoconazole (i.e., 12.5 mg/kg, ip), while "Alp 1" represents the number of cocaine infusions self-administered following the delivery of the ineffective dose of alprazolam (i.e., 1 mg/kg, ip). "Keto/Alp" represents the number of cocaine infusions self-administered following pretreatment with the combination of the ineffective doses of ketoconazole and alprazolam. Clearly, this combination significantly reduced cocaine self-administration regardless of the dose of cocaine that was available for self-administration. This indicates that the effects of the combination pharmacotherapy would not easily be overcome by increasing the intake or dose of cocaine.

Figure 5:
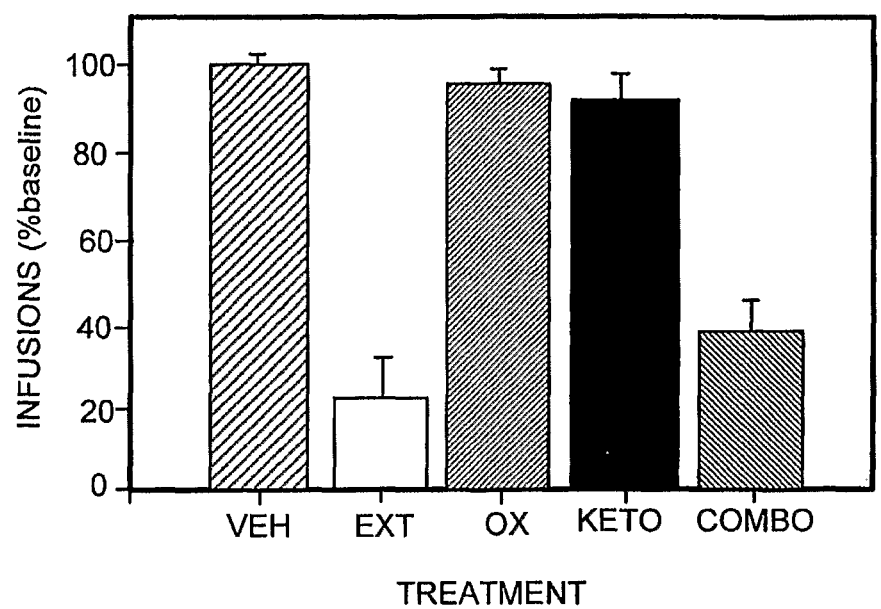
FIG. 5 is a bar graph illustrating the effect of the combination of ketoconazole and oxazepam on intravenous cocaine self-administration in rats. The infusion are expressed as a percentage of baseline.

The Effect of Ketoconazole and Oxazepam on Intravenous Self-Administration of Cocaine:

These experiments were designed to determine the effects of a combination of ketoconazole and oxazepam on intravenous cocaine self-administration in rats responding under a multiple, alternating schedule of food reinforcement and cocaine self-administration. Referring to FIG. 5, the solid bar "VEH") depicts the number of cocaine infusions self-administered following pretreatment with the vehicle (5% emulphor in 0.9% saline) for the treatment drugs. The open bar ("EXT") shows the results of extinction when responding on the "active" lever only resulted in infusions of saline. The striped bar ("OX") and the shaded bar ("KETO") represent self-administration following pretreatment with the low, ineffective doses (oxazepam 10 mg/kg, ip; ketoconazole 12.5 mg/kg, ip) of oxazepam and ketoconazole alone. These doses did not significantly affect cocaine self-administration (or food-maintained responding) when administered alone. The small-striped bar ("COMBO") depicts the number of cocaine infusions self-administered following the delivery of the combination pharmacotherapy (i.e., an injection consisting of the ineffective doses of oxazepam and ketoconazole). As can be seen in FIG. 5, the combination pharmacotherapy consisting of oxazepam and ketoconazole reduced cocaine self-administration to levels seen when only saline was delivered when the active lever was pressed during extinction. The combination pharmacotherapy reduced cocaine self-administration to extinction levels without affecting food-maintained responding, suggesting that the combination was reducing the motivation to seek cocaine without affecting responding or motivation for another reinforcer (i.e., food). These data further demonstrate that the effects of the combination pharmacotherapy are observed with different corticosterone synthesis inhibitors and different benzodiazepines.

Figure 6:
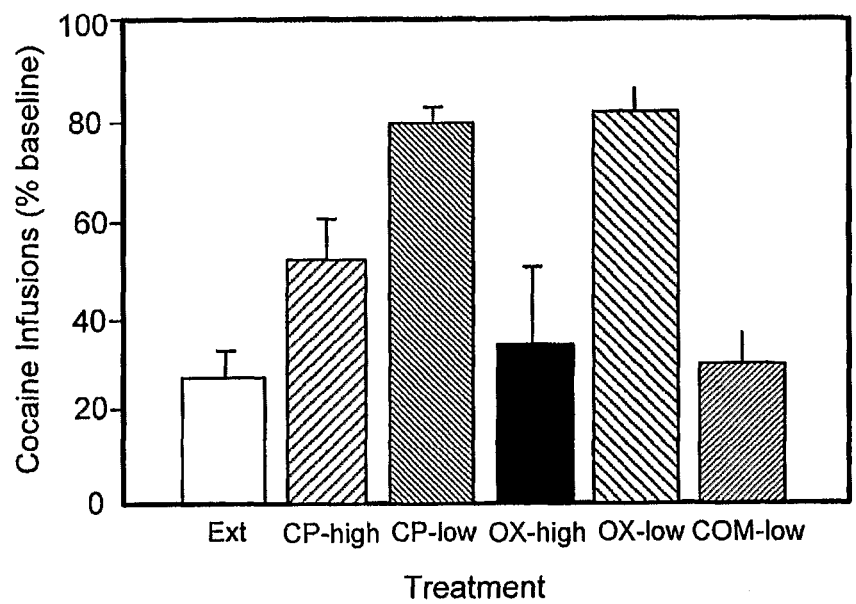
FIG. 6 is a bar graph illustrating the effect of the combination of CP-154,526 and oxazepam on intravenous cocaine self-administration in rats. The infusions are expressed as a percentage of baseline.

The Effect of CP-154,526 and Oxazepam on Intravenous Self-Administration of Cocaine:

These experiments were designed to determine the effects of a combination of CP-154,526 and oxazepam on intravenous cocaine self-administration in rats responding under a multiple, alternating schedule of food reinforcement and cocaine self-administration. The results are presented in FIG. 6 as the percentage of baseline infusions under the conditions tested. The white bar ("Ext") shows the results of extinction when responding on the "active" lever only resulted in infusions of saline. The bar labeled "CP-high" depicts the number of infusions self-administered following pretreatment with the high dose of CP-154,526 (10-80 mg/kg, ip), while the "OX-high" bar depicts the number of cocaine infusions self-administered following pretreatment with the high dose of oxazepam (5-25 mg/kg, ip). Both CP-154,526 and oxazepam reduced cocaine self-administration without affecting food-maintained responding at these doses. The "CP-low" and "OX-low" bar represent responding following pretreatment with the low, ineffective doses (CP-154,526, 5-25 mg/kg, ip; oxazepam, 5-25 mg/kg, ip) of CP-154,526 and oxazepam alone. These doses did not significantly affect cocaine self-administration or food-maintained responding when administered alone. The "COM-low" bar depicts the number of cocaine infusions self-administered following the delivery of the combination pharmacotherapy (i.e., an injection consisting of the ineffective doses of CP-154,526 and oxazepam). As can been seen from FIG. 6, the combination pharmacotherapy consisting of CP-154,526 and oxazepam reduced cocaine self-administration to levels seen when only saline was delivered when the active lever was pressed during extinction. The combination pharmacotherapy reduced cocaine self-administration to extinction levels without affecting food-maintained responding, suggesting that the combination was reducing the motivation to seek cocaine without responding or motivation for another reinforcer (i.e., food). These data also demonstrate that the effects of the combination pharmacotherapy are observed with the combination of a benzodiazepine and a CRH receptor antagonist.

Figure 7:
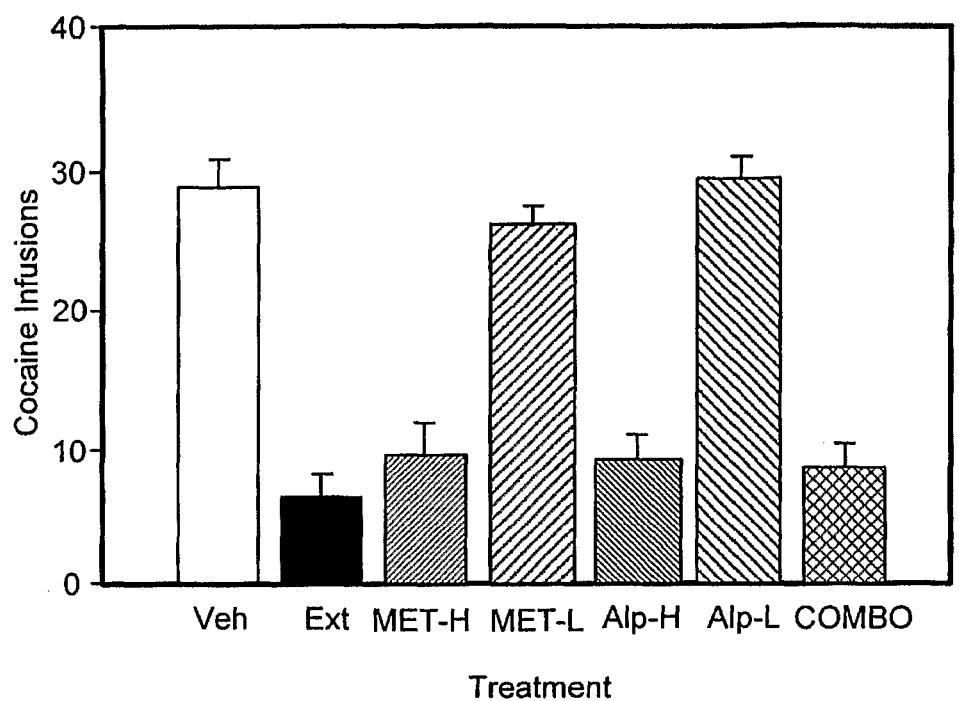
FIG. 7 is a bar graph illustrating the effect of the combination of metyrapone and alprazolam on intravenous cocaine self-administration in rats.

The Effect of Metyrapone and Alprazolam on Intravenous Self-Administration of Cocaine:

These experiments were designed to determine the effects of a combination of metyrapone and alprazolam on intravenous cocaine self-administration in rats responding under a multiple, alternating schedule of food reinforcement and cocaine self-administration. Referring to FIG. 7, the left-most bar ("Veh") depicts the number of cocaine infusions self-administered following pretreatment with the vehicle (5% emulphor in 0.9% saline) for the treatment drugs. The bar labeled "Ext" shows the results of extinction when responding on the "active" lever only resulted in infusions of saline. The "Met-H" bar shows the number of cocaine infusions self-administered following pretreatment with the high dose of metyrapone (25-175 mg/kg, ip), while the "ALP-H" bar depicts the number of cocaine infusions self-administered following pretreatment with the high dose of alprazolam (1-5 mg/kg, ip). Both metyrapone and alprazolam reduced cocaine self-administration without affecting food-maintained responding at these doses. The "Met-L" and "ALP-L" bars represent responding following pretreatment with the low, ineffective doses (metyrapone, 25-50 mg/kg, ip; alprazolam 0.5-2 mg/kg, ip) of metyrapone and alprazolam alone. These doses did not significantly affect cocaine self-administration or food-maintained responding when administered alone. The "COMBO" bar depicts the number of cocaine infusions self-administered following the delivery of the combination pharmacotherapy (i.e., an injection consisting of the ineffective doses of metyrapone and alprazolam). The combination pharmacotherapy consisting of metyrapone and alprazolam reduced cocaine self-administration to levels seen when only saline was delivered when the active lever was pressed during extinction. The combination pharmacotherapy reduced cocaine self-administration to extinction levels without affecting food-maintained responding suggesting that the combination was reducing the motivation to seek cocaine without affecting responding or motivation for another reinforcer (i.e., food).

Figure 8:
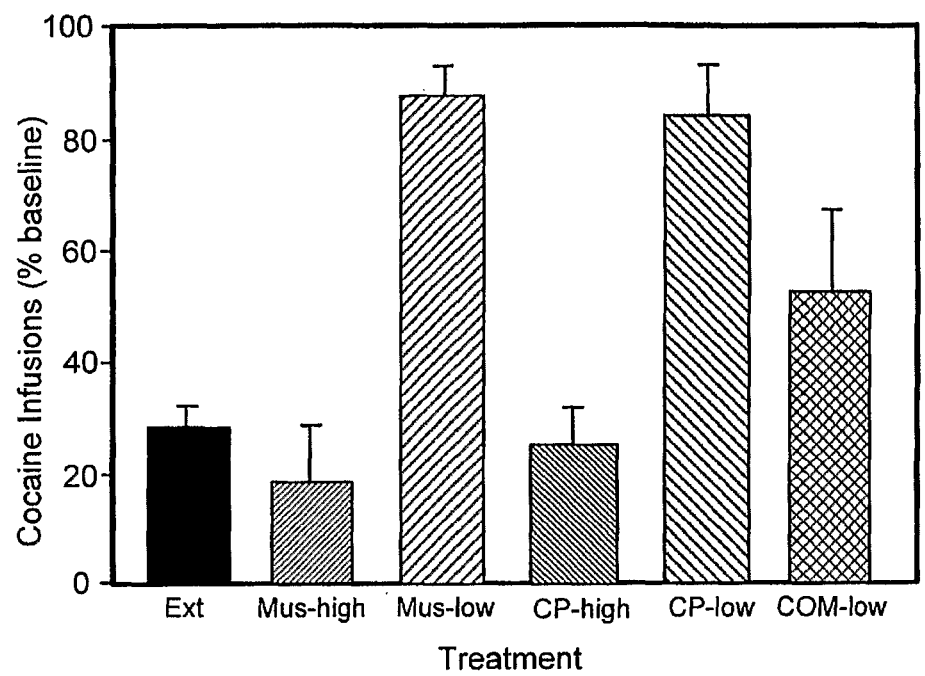
FIG. 8 is a bar graph illustrating the effect of the combination of muscimol and CP-154,526 on intravenous cocaine self-administration in rats. The infusions are expressed as a percentage of baseline.

The Effect of Muscimol and CP-154,526 on Intravenous Self-Administration of Cocaine:

These experiments were designed to determine the effects of a combination of CP-154,526 and muscimol on intravenous cocaine self-administration in rats responding under a multiple, alternating schedule of food reinforcement and cocaine self-administration. The results are shown in FIG. 8. The bar labeled "Ext" depicts the results of extinction when responding on the "active" lever only resulted in infusions of saline. The "Mus-high" bar shows the number of infusions self-administered following pretreatment with the high dose of muscimol (1-4 mg/kg, ip), while the "CP-high" bar depicts the number of cocaine infusions self-administered following pretreatment with the high dose of CP-154,526 (10-80 mg/kg, ip). Both muscimol and CP-154,526 reduced cocaine self-administration at these doses without affecting food-maintained responding. The "Mus-low" and "CP-low" bars represent responding following pretreatment with the low, ineffective doses of muscimol (0.5-2.0 mg/kg, ip) and CP-154,526 (5-25 mg/kg, ip) alone. These doses did not significantly affect cocaine self-administration of food-maintained responding when administered alone. The "COM-low" bar depicts the number of cocaine infusions self-administered following the delivery of the combination pharmacotherapy (i.e., an injection consisting of the ineffective doses of muscimol and CP-154,526). As can been seen in FIG. 8, the combination pharmacotherapy consisting of muscimol and CP-154,526 reduced cocaine self-administration close to levels seen when only saline was delivered when the active lever was pressed during extinction. The combination pharmacotherapy reduced cocaine self-administration close to extinction levels without affecting food-maintained responding, suggesting that the combination reduced the motivation to seek cocaine without affecting responding or motivation for another reinforcer (i.e., food).

Figure 9:
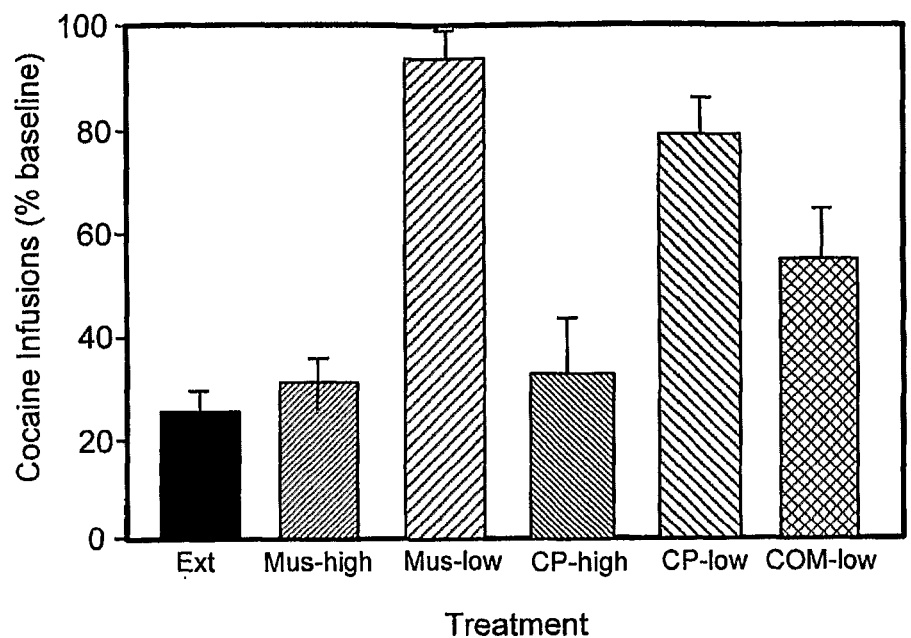
FIG. 9 is a bar graph illustrating the effect of the combination of muscimol and metyrapone on intravenous cocaine self-administration in rats. The infusions are expressed as a percentage of baseline.

The Effect of Muscimol and Metyrapone on Intravenous Self-Administration of Cocaine:

These experiments were designed to determine the effects of a combination of muscimol and metyrapone on intravenous cocaine self-administration in rats responding under a multiple, alternating schedule of food reinforcement and cocaine self-administration. The results are shown in FIG. 9. The bar labeled "Ext" depicts the results of extinction when responding on the "active" lever only resulted in infusions of saline. The "Mus-high" bar shows the number of infusions self-administered following pretreatment with the high dose of muscimol (1-4 mg/kg, ip), while the "Met-high" bar depicts the number of cocaine infusions self-administered following pretreatment with the high dose of metyrapone (25-175 mg/kg, ip). Both muscimol and metyrapone reduced cocaine self-administration at these doses without affecting food-maintained responding. The "Mus-low" and "Met-low" bars represent responding following pretreatment with the low, ineffective doses of muscimol (0.5-2.0 mg/kg, ip) and metyrapone (25-50 mg/kg, ip) alone. These doses did not significantly affect cocaine self-administration of food-maintained responding when administered alone. The "COM-low" bar depicts the number of cocaine infusions self-administered following the delivery of the combination pharmacotherapy (i.e., an injection consisting of the ineffective doses of muscimol and metyrapone). As can been seen in FIG. 9, the combination pharmacotherapy consisting of muscimol and metyrapone reduced cocaine self-administration close to levels seen when only saline was delivered when the active lever was pressed during extinction. The combination pharmacotherapy reduced cocaine self-administration close to extinction levels without affecting food-maintained responding, suggesting that the combination of a $GABA_A$ receptor agonist and a corticosterone synthesis inhibitor reduced the motivation to seek cocaine without affecting responding or motivation for another reinforcer (i.e., food).

Figure 11:
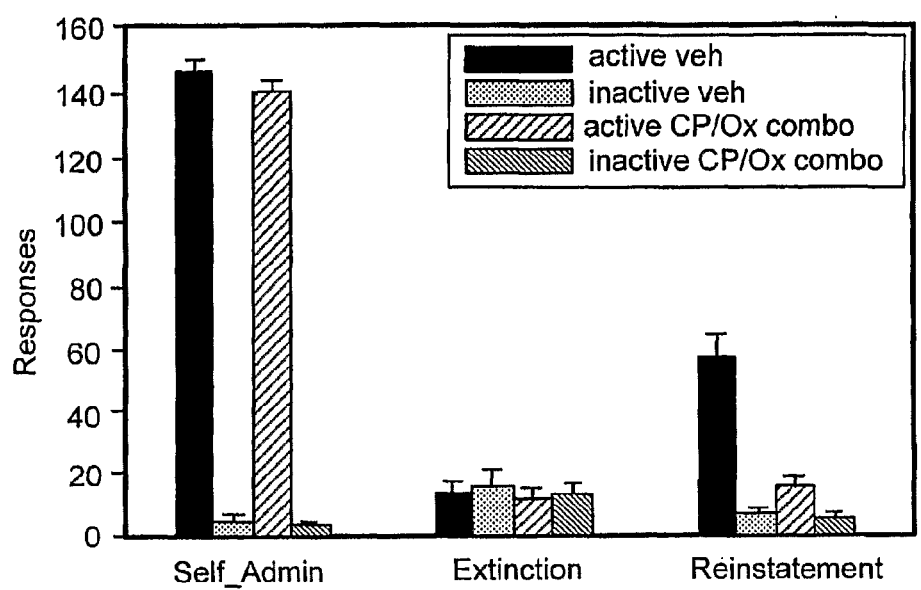
FIG. 11 is a bar graph illustrating the effect of chronic injections of metyrapone on the cue-induced reinstatement of extinguished cocaine-seeking behavior in rats.

The Effect of Chronic Injections of Metyrapone on the Cue-Induced Reinstatement of Extinguished Cocaine-Seeking Behavior:

These experiments were designed to determine the effects of the chronic administration of metyrapone on the cue-induced reinstatement of extinguished cocaine seeking in rats. We used a model of the relapse to cocaine seeking. This is an important experiment since the combination pharmacotherapy would be administered to cocaine addicts on a chronic basis. Referring to FIG. 11, the bar labeled "SA" depicts the number of responses made on the "active" lever during cocaine self-administration. The bar labeled "EXT" depicts the number of responses on the "active" lever during extinction when responding on this lever only resulted in infusions of saline. The bar labeled "VEH" represents responding on the "active" lever during reinstatement testing following pretreatment with the vehicle (5% emulphor in 0.9% saline). The bar labeled "Metyrapone" depicts the number of responses on the "active" lever during reinstatement testing following the chronic delivery of metyrapone (50 mg/kg, ip, once per day for 14 days). As can be seen in FIG. 11, the chronic administration of metyrapone reduced cocaine seeking to levels seen when only saline was delivered then the active lever was pressed during extinction. These data demonstrate that metyrapone remains effective in blocking the relapse of cocaine seeking following chronic administration.

Figure 12:
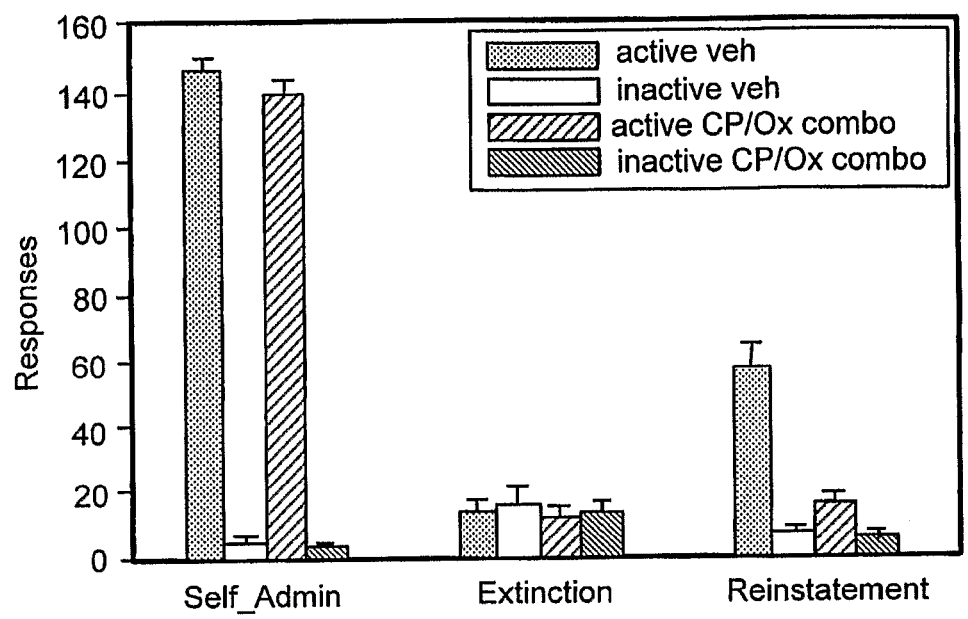
FIG. 12 is a bar graph illustrating the effect of CP-154,526 and oxazepam on the cue-induced reinstatement of extinguished cocaine-seeking behavior in rats.

Effects of the Combination of CP-154,526 and Oxazepam on the Cue-Induced Reinstatement of Extinguished Cocaine-Seeking Behavior:

These experiments were designed to determine the effects of a combination of CP-154,526 and oxazepam on the cue-induced reinstatement of extinguished cocaine seeking in rats. Referring to FIG. 12, the set of bars labeled "Self-Admin" depict the number of responses made on the "active" lever and a second "inactive" lever during cocaine self-administration. The first two bars in the set represent the responses of rats that eventually received the vehicle (5% emulphor in 0.9% saline) as treatment drugs during reinstatement testing. The third and fourth bars depict the response of rats that eventually received the combination pharmacotherapy (i.e., an injection consisting of the ineffective doses of CP-154,526 and oxazepam as determined in the cocaine self-administration experiments) during reinstatement testing. The rats were only injected with the vehicle or the combination pharmacotherapy once, which was 30 minutes before the start of the session for reinstatement testing. The responses during self-administration and extinction are only presented in FIG. 12 to demonstrate that there were no significant differences in responding between the groups. Responding on the "inactive" lever produced no programmed consequences at any time. The second set of bars, labeled "Extinction", depicts the number of responses on the "active" and "inactive" levers during extinction when responding on the "active" lever only resulted in infusions of saline. The third set of bars, labeled "Reinstatement", depicts the number of responses on the "active" and "inactive" levers during reinstatement testing following the delivery of the combination pharmacotherapy (i.e., an injection consisting of the ineffective doses of CP-154,526 and oxazepam as determined in the cocaine self-administration experiments). As can be clearly seen, the combination pharmacotherapy consisting of CP-154,526 and oxazepam reduced cocaine seeking (i.e., responding on the active lever during reinstatement) to levels seen when only saline was delivered when the active lever was pressed during extinction. The combination pharmacotherapy reduced reinstatement (relapse) to extinction levels without affecting food-maintained responding. This suggests that the combination reduced the motivation to seek cocaine without affecting responding or motivation for another reinforcer (i.e., food).

No Evidence of Pharmacokinetic Interaction Between Cocaine, Metyrapone, and Oxazepam:

Adult male Wistar rats (90 to 120 days old) were implanted with chronic, indwelling jugular catheters and were allowed to recover from surgery. On the test day, the rats were pretreated with intraperitoneal injections of various combinations of oxazepam and metyrapone (as indicated in the table of FIG. 14) or vehicle (5% emulphor in saline) 30 minutes before the cocaine injections were administered. The oxazepam/metyrapone combinations were selected from our behavioral studies that demonstrated that these combinations reduced cocaine self-administration or the cue-induced reinstatement of extinguished cocaine seeking without affecting food-maintained responding. Thirty minutes following the drug combination or vehicle injection, the rats received intravenous injections of cocaine (0.25 mg/kg/infusion) every 2 minutes for 1 hour. After the final injection of cocaine, blood was collected from the catheter for the analysis of cocaine and its metabolites ecgonine methyl ester and benzoylecgonine. Concentrations of metyrapone and metyrapol as well as oxazepam were also determined. All drug concentrations were determined using GCMS procedures. The results of these studies demonstrated that the combinations of oxazepam and metyrapone had no effect on the plasma concentrations of cocaine or its metabolites. These studies also demonstrated that metyrapone and oxazepam did not influence plasma concentrations of each other. Furthermore, the presence of cocaine did not affect the plasma concentrations of metyrapone or oxazepam. These data suggest that the behavioral effects we have observed in rats are not due to pharmacokinetic interactions among the various drugs.

A Combination of Oxazepam and Metyrapone Tested in the Forced Swim Test, an Animal Model of Depression:

The Forced Swim Test (FST) is an animal-model that possesses predictive validity for assessing a drug's anti-depressive efficacy. The subject is exposed to an inescapable, life-threatening situation to elicit learned helplessness. To achieve this, rats are placed in a cylinder filled with water from which they cannot escape and in which they must swim to stay afloat. At a point in time when the rat 'realizes' its situation is hopeless, despair-like behavior appears and rather than attempting to escape or swim, the rat becomes immobile. The time in this immobility posture is the behavior that is measured as despair. Oxazepam, a benzodiazepine, and metyrapone, an 11-β-hydroxylase inhibitor of corticosterone synthesis, have been shown to have anxiolytic and anti-depressant efficacy, respectively. The potential antidepressant properties of oxazepam and metyrapone administered alone and together both acutely and chronically were evaluated in male Wistar rats using the FST. Rats were injected with one of the drugs (5 or 10 mg/kg oxazepam, 25 or 50 mg/kg metyrapone) or combinations thereof both on day one after testing and again on day two before testing (acute) or for fourteen days before initiating testing on day one (chronic). The acute and chronic administrations of the drugs, alone and in combination, were effective in reducing immobility in the FST, indicating that this pharmacotherapy has antidepressant activity.

Learned helplessness is the construct on which the validity of using the FST as a model of depression is based. In humans, learned helplessness is often manifested as a symptom of depression, which appears as a loss of coping ability. For that reason we believe that drugs that have the effect of decreasing the time of immobility in the FST have potential as candidates for lessening the loss of coping ability seen in the human model of depression. In the current studies, oxazepam and metyrapone were tested alone and in combination in the FST to determine whether these agents might show antidepressant activity.

The parameters of the study were outlined above. More specifically, male Wistar rats from Harlan weighing 275-400 grams were used. The rats were allowed to acclimate at least one day in the Animal Resources Facility after arrival before being tested. To perform the FST, a Plexiglas cylinder (40 cm tall×18 cm diameter) was filled with fresh, 25° C. water to a depth of 20 cm, which is deep enough so the rat cannot touch bottom, yet far enough from the rim to prevent the rat from escaping. Rats were injected intraperitoneally with either vehicle, drugs, or combinations of oxazepam and metyrapone on day one after testing and again on day two before testing (acute) or for fourteen days before initiating testing on day one (chronic). On day one, the rat was removed from his cage, placed in the water, and observed for fifteen minutes. Generally, for the first few minutes, the rat would swim around with his paws thrashing above the water line, sniff, dive, and attempt to jump out of the cylinder. Such actions were deemed escape-oriented behavior. Following the escape-oriented behavior was a time characterized by the rat discontinuing its attempts to escape. Generally, the rat would either tread water, exerting only enough energy to keep its head above water, or would float with only its nose above the water line. This second phase of behavior was deemed the immobility posture. Length of time spent in escape-oriented behavior and immobility posture was recorded. Then the rat was removed from the water, dried with a towel, and returned to his home cage. On day two the procedure was repeated for five minutes and the time spent engaging in escape-oriented behavior and immobility posture were recorded. The second day's duration of immobility was compared among the different groups. Dosage groups were compared to the vehicle-injected controls using a one way ANOVA with $p<0.05$. If the Immobility Time for a drug group was statistically significant compared to that of the vehicle group, the drug combination was considered to exhibit an antidepressant-like effect.

The effects of the chronic administration of oxazepam and metyrapone were more profound in the combination-treated groups. Only one group to which individual drugs were administered, the Met50 group, showed a lessening of immobility time. This is suggestive of a synergistic action when both drugs are administered simultaneously. Perhaps this synergistic effect can be explained by an increase in oxazepam's agonistic action on the $GABA_A$ receptor induced by the metabolic by-products of metyrapone. When metyrapone inhibits corticosterone synthesis, the concentrations of two precursors upstream of corticosterone, 11-Deoxycorticosterone (11-DOC) and Progesterone (Prog), increase. This increase may shunt the pathway towards the production of $GABA_A$-active neurosteroids such as allopregnanolone and tetrahydrodeoxycorticosterone. These two neurosteroids bind allosterically to the $GABA_A$ receptor resulting in an increase of Cl-flowing into the cell, thus causing hyperpolarization and decreased neuronal excitability. The possible outcome is that both oxazepam (by direct binding) and metyrapone (indirectly through neurosteroids) both influence $GABA_A$ currents via allosteric mechanisms. Regardless of the mechanism of action, it is clear that the combination of Ox10/Met50 elicited the largest reduction in immobility time. Tolerance appears to have formed in the chronically treated groups, especially to those groups who received only Ox or Met. This is evident by the observation that the means for these groups were equal to or exceeded the vehicle.

A number of embodiments of the invention have been described. Nevertheless, it will be understood that various modifications may be made without departing from the spirit and scope of the invention. Accordingly, other embodiments are within the scope of the following claims.

What is claimed is:

1. A pharmaceutical composition for the treatment of addiction consisting essentially of a first agent that targets the hypothalamo-pituitary-adrenal (HPA) axis and down-regulates the effect of cortisol in a subject to whom the composition is administered, wherein the first agent is metyrapone or a pharmaceutically acceptable salt thereof, and a second agent wherein the second agent is oxazepam or a pharmaceutically acceptable salt thereof, wherein said pharmaceutical composition is a single combination dosage form, and
wherein both the first agent and the second agent are present within the composition in an amount that is ineffective to treat addiction when either the first agent or the second agent is administered alone.

2. The pharmaceutical composition of claim 1 consisting essentially of about 5-60 mg of oxazepam and about 5-1500 mg of metyrapone in unit dosage form.

3. A pharmaceutical composition for the treatment of addiction consisting essentially of: (a) a first agent that targets the hypothalamo-pituitary-adrenal (HPA) axis and down-regulates the effect of cortisol in a subject to whom the composition is administered, wherein the first agent is metyrapone or a pharmaceutically acceptable salt thereof, (b) a second agent wherein the second agent is oxazepam or a pharmaceutically acceptable salt thereof, and (c) one or more inactive agents, wherein the one or more inactive agents comprises a carrier or excipient, a preservative, or a substance that increases the solubility of the first agent or the second agent, and wherein said pharmaceutical composition is a single combination dosage form,
wherein both the first agent and the second agent are present within the composition in an amount that is ineffective to treat addiction when either the first agent or the second agent is administered alone.

4. The pharmaceutical composition of claim 3, wherein said composition is in unit dosage form, and wherein the first agent is metyrapone in a dosage of about 5-1500 mg, and the second agent is oxazepam in a dosage of about 5-60 mg.

5. The pharmaceutical composition of claim 2, wherein the ratio of the first agent to the second agent is about 100:1, 90:1, 80:1, 75:1, 70:1, 65:1, 60:1, 55:1, 50:1, 45:1, 40:1, 35:1, 30:1, 25:1, 20:1, 15:1, 10:1, 9:1, 8:1, 7:1, 6:1, 5:1, 4:1, 3:1, 2:1, or about 1:1.

6. The pharmaceutical composition of claim 4, wherein the ratio of the first agent to the second agent is about 100:1, 90:1, 80:1, 75:1, 70:1, 65:1, 60:1, 55:1, 50:1, 45:1, 40:1, 35:1, 30:1, 25:1, 20:1, 15:1, 10:1, 9:1, 8:1, 7:1, 6:1, 5:1, 4:1, 3:1, 2:1, or about 1:1.

7. The pharmaceutical composition of claim 2, wherein the dosage of metyrapone is about 25-1500 mg, 50-1250 mg, 100-1250 mg, 100-1000 mg, 250-1000 mg, 500-1000 mg or 750-1000 mg; and
wherein dosage of oxazepam is about 5-50 mg, about 5-40 mg, about 5-30 mg, about 5-20 mg, about 5-10 mg, about 10-50 mg, about 10-40 mg, about 10-30 mg, about 20-50 mg, about 20-40 mg, about 20-30 mg, about 30-50 mg or about 30-40 mg.

8. The pharmaceutical composition of claim 4,
wherein the dosage of metyrapone is about 25-1500 mg, 50-1250 mg, 100-1250 mg, 100-1000 mg, 250-1000 mg, 500-1000 mg or 750-1000 mg; and
wherein dosage of oxazepam is about 5-50 mg, about 5-40 mg, about 5-30 mg, about 5-20 mg, about 5-10 mg, about 10-50 mg, about 10-40 mg, about 10-30 mg, about 20-50 mg, about 20-40 mg, about 20-30 mg, about 30-50 mg or about 30-40 mg.

9. The pharmaceutical composition of claim 2,
wherein the dosage of metyrapone is about 5, 10, 25, 50, 100, 200, 250, 300, 400, 450, 500, 550, 600, 650, 700, 750, 800, 850, 900, 1000, 1250, or 1500 mg; and
wherein dosage of oxazepam is about 1, 5, 10, 20, 25, 30, 35, 40, 45, 50 mg.

10. The pharmaceutical composition of claim 4,
wherein the dosage of metyrapone is about 5, 10, 25, 50, 100, 200, 250, 300, 400, 450, 500, 550, 600, 650, 700, 750, 800, 850, 900, 1000, 1250, or 1500 mg; and
wherein dosage of oxazepam is about 1, 5, 10, 20, 25, 30, 35, 40, 45, 50 mg.

11. The pharmaceutical composition of claim 2, wherein the composition consists essentially of:
(i) 270 mg metyrapone and 12 mg oxazepam;
(ii) 540 mg metyrapone and 24 mg oxazepam; or
(iii) 720 mg metyrapone and 24 mg oxazepam.

12. The pharmaceutical composition of claim 3, wherein the composition consists of:
(i) 270 mg metyrapone and 12 mg oxazepam;
(ii) 540 mg metyrapone and 24 mg oxazepam; or
(iii) 720 mg metyrapone and 24 mg oxazepam.

* * * * *